(12) United States Patent
Roed et al.

(10) Patent No.: US 11,753,455 B2
(45) Date of Patent: Sep. 12, 2023

(54) COMPOUNDS FOR TREATMENT OF OBESITY

(71) Applicant: Novo Nordisk A/S, Bagsvaerd (DK)

(72) Inventors: Nikolaj Kulahin Roed, Birkeroed (DK); Michael Paolo Bastner Sandrini, Alleroed (DK); Jesper Lau, Farum (DK); Paw Bloch, Jyllinge (DK); Anna Secher, Koebenhavn NV (DK); Adam Paul Chambers, Alleroed (DK); Jim McGuire, Berkeley, CA (US); Lotte Bjerre Knudsen, Jerslev (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 17/253,708

(22) PCT Filed: Jun. 20, 2019

(86) PCT No.: PCT/EP2019/066358
§ 371 (c)(1),
(2) Date: Dec. 18, 2020

(87) PCT Pub. No.: WO2019/243502
PCT Pub. Date: Dec. 26, 2019

(65) Prior Publication Data
US 2021/0261641 A1   Aug. 26, 2021

(30) Foreign Application Priority Data

Jun. 21, 2018   (EP) .................................. 18179022

(51) Int. Cl.
*C07K 14/575*   (2006.01)
*A61K 47/62*   (2017.01)
*A61K 38/00*   (2006.01)

(52) U.S. Cl.
CPC ............ *C07K 14/575* (2013.01); *A61K 47/62* (2017.08); *A61K 38/00* (2013.01); *C07K 2319/74* (2013.01)

(58) Field of Classification Search
CPC .. C07K 14/575; C07K 2319/74; A61K 47/62; A61K 38/00
See application file for complete search history.

(56) References Cited

U.S. PATENT DOCUMENTS

| | | | |
|---|---|---|---|
| 9,994,641 B2 | 6/2018 | Sonoda et al. | |
| 10,233,230 B2 | 3/2019 | Hwang et al. | |
| 10,266,577 B2 | 4/2019 | Sauerberg et al. | |
| 2006/0130158 A1 | 6/2006 | Turner et al. | |
| 2006/0205037 A1* | 9/2006 | Sadeghi | C07K 14/605 |
| | | | 514/1.2 |
| 2009/0239795 A1 | 9/2009 | Ballance et al. | |
| 2010/0077498 A1 | 3/2010 | Pardridge et al. | |
| 2015/0291704 A1* | 10/2015 | Beck | C07K 16/065 |
| | | | 435/68.1 |
| 2016/0024169 A1* | 1/2016 | Dimarchi | C07K 14/605 |
| | | | 530/303 |
| 2016/0136246 A1 | 5/2016 | Christiansen | |
| 2016/0143998 A1* | 5/2016 | Reedtz-Runge | A61P 25/30 |
| | | | 530/308 |
| 2017/0174777 A1* | 6/2017 | Barbour | C07K 16/28 |
| 2018/0171012 A1 | 6/2018 | Sonoda et al. | |

FOREIGN PATENT DOCUMENTS

| | | |
|---|---|---|
| CN | 102268094 A | 12/2011 |
| CN | 105324126 A | 2/2016 |
| CN | 105451776 A | 3/2016 |
| CN | 107106660 A | 8/2017 |
| JP | 2008531059 A | 8/2009 |
| WO | 2004019872 A2 | 3/2004 |
| WO | 2006017688 A2 | 2/2006 |
| WO | 2006096515 | 9/2006 |
| WO | 2008033395 A2 | 3/2008 |
| WO | 2009121804 A1 | 10/2009 |
| WO | 2010108937 A2 | 9/2010 |
| WO | 2011039096 A1 | 4/2011 |

(Continued)

OTHER PUBLICATIONS

Yu et al., "Boosting Brain Uptake of a Therapeutic Antibody by Reducing its Affinity for a Transcytosis Target," Science Translational Medicine, May 2011, vol. 3, No. 84, pp. 1-8.
Van Bloemendaal et al., "Effects of glucagon-like peptide 1 on appetite and body weight: focus on the CNS," Journal of Endocrinology, Apr. 2014, vol. 221, No. 1, pp. T1-T16.
"Anonymous: ""JCR to Initiate Development of a New Drug Candidate for Sanfilippo Syndrome Type A Using J-Brain Cargo,""" Contify Life Science News, Feb. 23, 2017, XP055531402, Retrieved from the Internet: URL:http://www.jcrpharm.co.jp/wp2/wpcontent/uploads/2017/02/cdd41f192f74c0791168c0982feee810.pdf [retrieved on Dec. 7, 2018]".

(Continued)

*Primary Examiner* — Amber D Steele
(74) *Attorney, Agent, or Firm* — Leon Y. Lum

(57) ABSTRACT

The invention relates to a construct comprising a compound targeting areas in the brain involved in the regulation of body weight and an allosteric ligand to a receptor located in the blood-brain barrier (BBB). The invention also relates to compositions and uses of such construct, for example in the prevention or treatment of overweight and obesity. Preferred compounds for regulation of body weight include GLP-1 receptor agonists (GLP-1RA), and preferred receptors located in the BBB include the transferrin receptor (TfR). Exemplary fusions and conjugates of GLP-1 RA's and anti TfR-Fab's exhibit an increased binding to brain regions expressing the GLP-1 receptor as compared to fusions or conjugates with inactive control Fab's, in particular in brain areas protected by the BBB. In vivo mice studies confirm increased reduction in food intake as well as weight loss for the active construct compared to the inactive one.

6 Claims, 10 Drawing Sheets

Specification includes a Sequence Listing.

(56) References Cited

FOREIGN PATENT DOCUMENTS

| WO | 2012075037 A1 | 6/2012 | | |
|---|---|---|---|---|
| WO | 2012136790 A1 | 10/2012 | | |
| WO | 2012136792 A2 | 10/2012 | | |
| WO | 2013177062 A2 | 11/2013 | | |
| WO | 2014033074 A1 | 3/2014 | | |
| WO | 2014189973 A2 | 11/2014 | | |
| WO | 2015098989 A1 | 7/2015 | | |
| WO | 2015101588 A1 | 7/2015 | | |
| WO | 2016077840 A2 | 5/2016 | | |
| WO | 2016081643 A1 | 5/2016 | | |
| WO | 2016208695 A1 | 12/2016 | | |
| WO | WO 2016/193380 | * | 12/2016 | ............. C07K 14/62 |
| WO | 2018026742 A1 | 2/2018 | | |

OTHER PUBLICATIONS

"Byung-Joon Kim et al, ""Transferrin Fusion Technology: A Novel Approach to Prolonging Biological Half-Life of Insulinotropic Peptides,"" Journal of Pharmacology and Experimental Therapeutics, American Society for Pharmacology and Experimental Therapeutics, Sep. 2010, vol. 334, No. 3, pp. 682-692".

Egan et al, "Glucagon-like peptide-1, fused to human transferrin, is a long-acting and potent anti-hyperglycemic agent," Diabetologia, 2005, vol. 48, pp. A202-A202, Supplement: 1, Meeting Abstract: 548.

Hiroyuki Sonoda et al, "A Blood-Brain-Barrier-Penetrating Anti-human Transferrin Receptor Antibody Fusion Protein for Neuronopathic Mucopolysaccharidosis II," Molecular Therapy : The Journal of the American Society of Gene Therapy, May 2018, vol. 26, No. 5, pp. 1366-1374.

Hunter et al., "Drugs developed to treat diabetes, liraglutide and lixisenatide, cross the blood brain barrier and enhance neurogenesis", Mar. 2012, BMC Neuroscience, Biomed Central, vol. 13, Article No. 33, pp. 1-6.

"Junyi Shen et al: 11 ""Ginsenoside Rg1 nanoparticle penetrating the blood-brain barrier to improve the cerebral function of diabetic rats complicated with cerebral infarction,"" International Journal of Nanomedicine, Jan. 2017, vol. 12, pp. 6477-6486".

"Lee et al., ""Receptor mediated uptake of peptides that bind the human transferrin receptor,"" Eur. J. Biochem, Dec. 2001, vol. 268, pp. 2004-2012".

"Liu et al., ""B6 Peptide-Modified PEG-PLA Nanoparticles for Enhanced Brain Delivery of Neuroprotective Peptide,"" Bioconjugate Chem., May 2013, vol. 24, pp. 997-1007".

Matsubara et al, "Single Dose GLP-1-Tf Ameliorates Myocardial Ischemia/Reperfusion Injury," Journal of Surgical Research, Jan. 2011, vol. 165, pp. 38-45.

Matsubara et al., "Glucagon-like-peptide-1 fused to transferrin: A novel approach to myocardial reperfusion injury," Journal of the American College of Cardiology, Mar. 2007, vol. 49, No. 9, pp. 236A-236A, Supplement: A.

Minzhi Yu et al, "Battle of GLP-1 delivery technologies," Advanced Drug Delivery Reviews, May 2018, vol. 130, pp. 113-130.

Pardridge et al., "Selective Transport of an Anti-transferrin Receptor Antibody through the Blood-Brain Barrier in Vivo," J. Pharm and experiment Therapeutics, 1991, vol. 259, No. 1, pp. 66-70.

"Paul J. Meakin et al: ""Reduction in BACE1 decreases body weight, protects against diet-induced obesity and enhances insulin sensitivity in mice""", Biochemical Journal, Jan. 2012, vol. 441, No. 1, pp. 285 296".

Prades et al., "Delivery of gold nanoparticles to the brain by conjugation with a peptide that recognizes the transferrin receptor," Biomaterials, Oct. 2012, vol. 33, No. 29, pp. 7194-7205.

"Richard D. Egleton et al, ""Development of neuropeptide drugs that cross the blood-brain barrier,"" Journal of the American Society for Experimental Neurotherapeutics, Jan. 2005, vol. 2, No. 1, pp. 44-53".

"Secher et al., ""The arcuate nucleus mediates GLP-1 receptor agonist liraglutide-dependent weight loss,"" Journal of Clinical Investigation, Sep. 2014, vol. 124, No. 10, pp. 4473-4488".

* cited by examiner

```
  1 DIQMTQSPASLSASLEEIVTITCQASQDIGNWLAWYQQKP
 41 GKSPQLLIYGATSLADGVPSRFSGSRSGTQFSLKISRVQV
 81 EDIGIYYCLQAYNTPWTFGGGTKLELKRTVAAPSVFIFPP
121 SDEQLKSGTASVVCLLNNFYPREAKVQWKVDNALQSGNSQ
161 ESVTEQDSKDSTYSLSSTLTLSKADYEKHKVYACEVTHQG
201 LSSPVTKSFNRGECEVQLVESGGGLVQPGNSLTLSCVASG
241 FTFSNYGMHWIRQAPKKGLEWIAMIYYDSSKMNYADTVKG
281 RFTISRDNSKNTLYLEMNSLRSEDTAMYYCAVPTSHYVVD
321 VWGQGVSVTVSSASTKGPSVFPLAPCSRSTSESTAALGCL
361 VKDYFPEPVTVSWNSGCLTSGVHTFPAVLQSSGLYSLSSV
401 VTVPSSSLGTKTYTCNVDHKPSNTKVDKRVESK
```

Fig. 1A

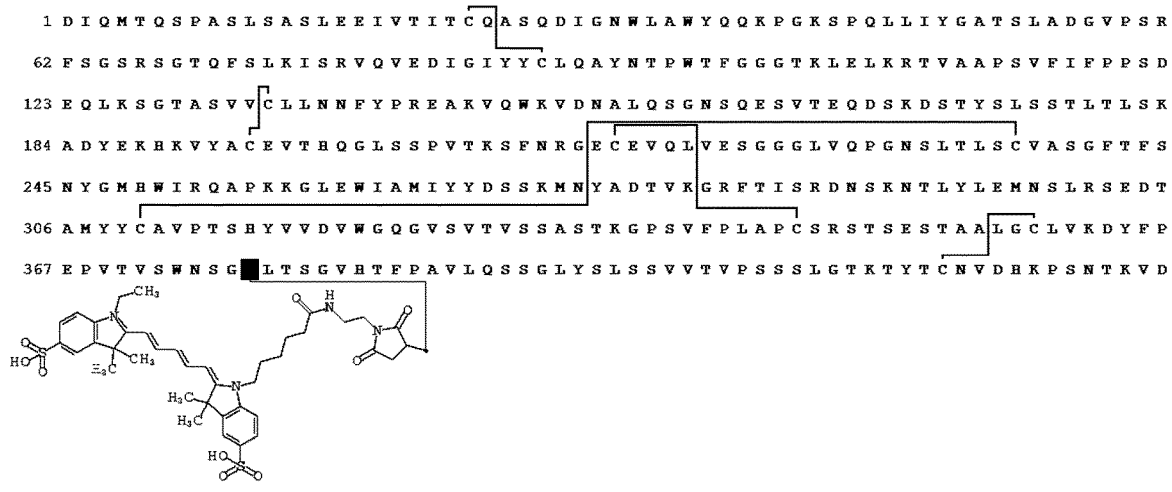

Fig. 1B

```
  1 DIVMTQTPLSLSVTPGQPASISCRSSQSLLHSNGNTYLHW
 41 YLQKPGQSPQLLIYKVSNRFSGVPDRFSGSGSGTDFTLKI
 81 SRVEAEDVGVYYCSQSTHVPWTFGQGTKVEIKRTVAAPSV
121 FIFPPSDEQLKSGTASVVCLLNNFYPREAKVQWKVDNALQ
161 SGNSQESVTEQDSKDSTYSLSSTLTLSKADYEKHKVYACE
201 VTHQGLSSPVTKSFNRGECEVQLVESGGGLVQPGNSLTLS
241 CVASGFTFSNYGMHWIRQAPKKGLEWIAMIYYDSSKMNYA
281 DTVKGRFTISRDNSKNTLYLEMNSLRSEDTAMYYCAVPTS
321 HYVVDVWGQGVSVTVSSASTKGPSVFPLAPCSRSTSESTA
361 ALGCLVKDYFPEPVTVSWNSGCLTSGVHTFPAVLQSSGLY
401 SLSSVVTVPSSSLGTKTYTCNVDHKPSNTKVDKRVESK
```

Fig. 2

```
  1 DIQMTQSPASLSASLEEIVTITCQASQDIGNWLAWYQQKP
 41 GKSPQLLIYGATSLADGVPSRFSGSRSGTQFSLKISRVQV
 81 EDIGIYYCLQAYNTPWTFGGGTKLELKRTVAAPSVFIFPP
121 SDEQLKSGTASVVCLLNNFYPREAKVQWKVDNALQSGNSQ
161 ESVTEQDSKDSTYSLSSTLTLSKADYEKHKVYACEVTHQG
201 LSSPVTKSFNRGECEVQLVESGGGLVQPGNSLTLSCVASG
241 FTFSNYGMHWIRQAPKKGLEWIAMIYYDSSKMNYADTVKG
281 RFTISRDNSKNTLYLEMNSLRSEDTAMYYCAVPTSHYVVD
321 VWGQGVSVTVSSASTKGPSVFPLAPCSRSTSESTAALGCL
361 VKDYFPEPVTVSWNSGCLTSGVHTFPAVLQSSGLYSLSSV
401 VTVPSSSLGTKTYTCNVDHKPSNTKVDKRVESK
```

Fig. 3

```
  1 DIVMTQTPLSLSVTPGQPASISCRSSQSLLHSNGNTYLHW
 41 YLQKPGQSPQLLIYKVSNRFSGVPDRFSGSGSGTDFTLKI
 81 SRVEAEDVGVYYCSQSTHVPWTFGQGTKVEIKRTVAAPSV
121 FIFPPSDEQLKSGTASVVCLLNNFYPREAKVQWKVDNALQ
161 SGNSQESVTEQDSKDSTYSLSSTLTLSKADYEKHKVYACE
201 VTHQGLSSPVTKSFNRGECEVQLVESGGGLVQPGNSLTLS
241 CVASGFTFSNYGMHWIRQAPKKGLEWIAMIYYDSSKMNYA
281 DTVKGRFTISRDNSKNTLYLEMNSLRSEDTAMYYCAVPTS
321 HYVVDVWGQGVSVTVSSASTKGPSVFPLAPCSRSTSESTA
361 ALGCLVKDYFPEPVTVSWNSGCLTSGVHTFPAVLQSSGLY
401 SLSSVVTVPSSSLGTKTYTCNVDHKPSNTKVDKRVESK
```

Fig. 4

```
  1 HGEGTFTSDVSSYLEEQAAREFIAWLVKGRPGGGSGGGSGGGSGGGSDIVMTQTPLSLSVT
 62 PGQPASISCRSSQSLLHSNGNTYLHWYLQKPGQSPQLLIYKVSNRFSGVPDRFSGSGSGTD
123 FTLKISRVEAEDVGVYYCSQSTHVPWTFGQGTKVEIKRTVAAPSVFIFPPSDEQLKSGTAS
184 VVCLLNNFYPREAKVQWKVDNALQSGNSQESVTEQDSKDSTYSLSSTLTLSKADYEKHKVY
245 ACEVTHQGLSSPVTKSFNRGECQVQLQESGPGLVKPSETLSLTCTVSGGSISSGYWNWIRQ
306 PPGKGLEWIGTISYSGDTYYNPSLKSRVTISVDTSKNQFSLKLSSVTAADTAVYYCARYGS
367 YVFDYWGQGTTVTVSSASTKGPSVFPLAPCSRSTSESTAALGCLVKDYFPEPVTVSWNSGA
428 LTSGVHTFPAVLQSSGLYSLSSVVTVPSSSLGTKTYTCNVDHKPSNTKVDKRVESKHHHH
489 HHHH
```

Fig. 5

1 HGEGTFTSDVSSYLEEQAAREFIAWLVKGRPGGGSGGGSGGGSGGGSDIQMTQSPASLSAS
62 LEEIVTITCQASQDIGNWLAWYQQKPGKSPQLLIYGATSLADGVPSRFSGSRSGTQFSLKI
123 SRVQVEDIGIYYCLQAYNTPWTFGGGTKLELKRADAAPTVSIFPPSSEQLTSGGASVVCFL
184 NNFYPKDINVKWKIDGSERQNGVLNSWTDQDSKDSTYSMSSTLTLTKDEYERHNSYTCEAT
245 HKTSTSPIVKSFNRNECEVQLVESGGGLVQPGNSLTLSCVASGFTFSNYGMHWIRQAPKKG
306 LEWIAMIYYDSSKMNYADTVKGRFTISRDNSKNTLYLEMNSLRSEDTAMYYCAVPTSHYVV
367 DVWGQGVSVTVSSAKTTPPSVYPLAPGSAAQTNSMVTLGCLVKGYFPEPVTVTWNSGSLSS
428 GVHTFPAVLQSDLYTLSSSVTVPSSTWPSETVTCNVAHPASSTKVDKKIVPRDCGHHHHHH
489 HHHH

Fig. 6

1 HGEGTFTSDVSSYLEEQAAREFIAWLVKGRPGGGSGGGSGGGSGGGSDIVMTQTPLSLSVT
62 PGQPASISCRSSQSLLHSNGNTYLHWYLQKPGQSPQLLIYKVSNRFSGVPDRFSGSGSGTD
123 FTLKISRVEAEDVGVYYCSQSTHVPWTFGQGTKVEIKRTVAAPSVFIFPPSDEQLKSGTAS
184 VVCLLNNFYPREAKVQWKVDNALQSGNSQESVTEQDSKDSTYSLSSTLTLSKADYEKHKVY
245 ACEVTHQGLSSPVTKSFNRGECEVQLVESGGGLVQPGNSLTLSCVASGFTFSNYGMHWIRQ
306 APKKGLEWIAMIYYDSSKMNYADTVKGRFTISRDNSKNTLYLEMNSLRSEDTAMYYCAVPT
367 SHYVVDVWGQGVSVTVSSAKTTPPSVYPLAPGSAAQTNSMVTLGCLVKGYFPEPVTVTWNS
428 GSLSSGVHTFPAVLQSDLYTLSSSVTVPSSTWPSETVTCNVAHPASSTKVDKKIVPRDCGH
489 HHHHHHHH

Fig. 7

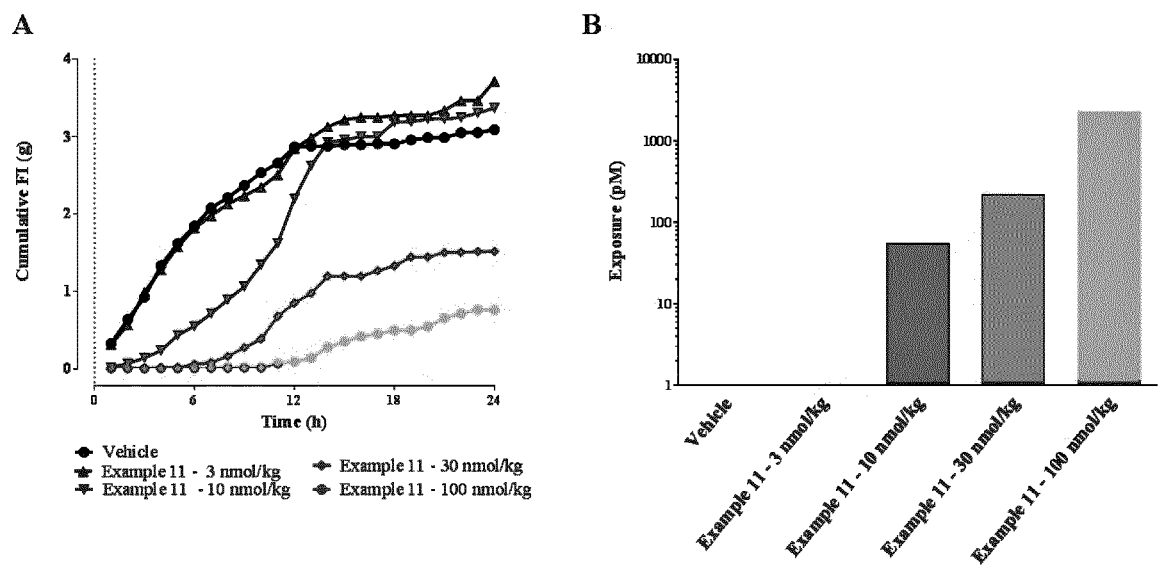
Fig. 17 A and B
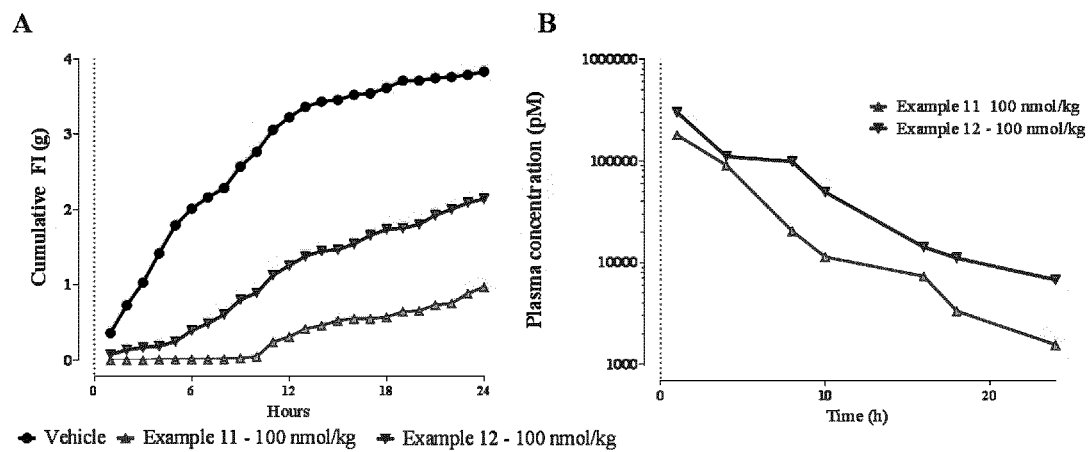
Fig. 18 A and B

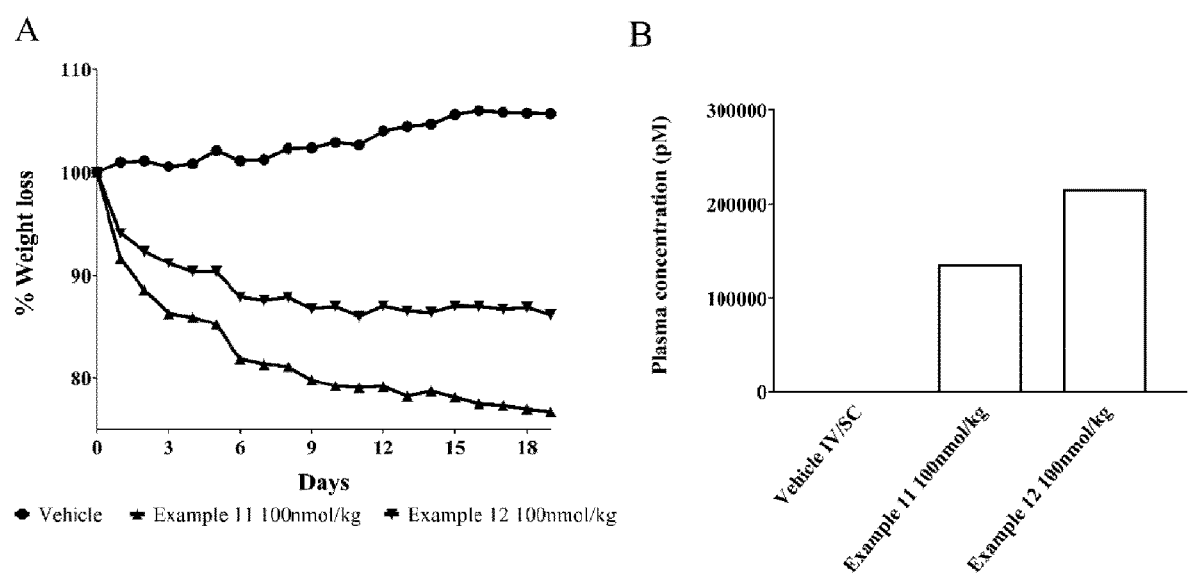
Fig. 19 A and B

COMPOUNDS FOR TREATMENT OF OBESITY

CROSS-REFERENCE TO RELATED APPLICATIONS

This application is a 35 U.S.C. § 371 National Stage application of International Application PCT/EP2019/066358 (WO/2019/243502), filed Jun. 20, 2019, which claims priority to European Patent Application 18179022.1, filed Jun. 21, 2018; the contents of which are incorporated herein by reference.

TECHNICAL FIELD

The present invention relates to novel compounds for treatment of obesity and related conditions.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on May 23, 2018, and amended on Jun. 23, 2022, is named "180007US01_sequence listing_ST25", and is 39 kilobytes in size.

BACKGROUND

Obesity is the result of a long-term positive energy balance whereby energy intake surpasses expenditure. The central nervous system (CNS) plays a major role in the maintenance of body weight within a narrow range by regulating energy intake. To regulate energy intake, signals, both neuronal and humoral, arising from peripheral organs involved in food intake convey information on hunger and/or satiety to the brain. Gut-derived hormones, such as prandially secreted glucagon like peptide 1 (GLP-1), have been identified as players in the regulation of feeding by relaying meal-related information on nutritional status to the brain (Journal of Endocrinology (2014), vol. 221(1), p. T1-T16).

The presence of GLP-1 receptors in the CNS and findings from animal and human studies indicate that the GLP-1 receptor agonist (GLP-1RA) induced satiety and weight effects are, at least in part, mediated by their actions on the brain, however, brain penetration of GLP-1 and GLP-1RA's is severely limited by the largely impermeable blood-brain barrier (BBB) (Journal of Clinical Investigation (2014), vol. 124(10), p. 4473-4488).

One approach to facilitate delivery of protein therapeutics across the BBB is to take advantage of receptor mediated transcytosis, an endogenous endocytic process in which a ligand is transported across an endothelial cell barrier. Among the many strategies to overcome this obstacle is to utilise transcytosis trafficking pathways of endogenous receptors expressed at the brain capillary endothelium such as the transferrin receptor (TfR) (Science Translational Medicine (2011), vol. 3(84), p. 1-8).

WO 2004/019872 A2 relates to pharmaceutical compositions comprising a transferrin (Tf) protein exhibiting reduced glycosylation fused to at least one therapeutic protein or peptide, and methods of using same. Prophetic Example 1 is entitled "GLP-1-transferrin fusion proteins".

The preparation of transferrin fusion proteins with analogues of GLP-1 and exendin-4 are disclosed in the article "Transferrin Fusion Technology: A Novel Approach to Prolonging Biological Half-Life of Insulinotropic Peptides" by Byung-Joon Kim et al, in Journal of Pharmacology and Experimental Therapeutics, Vol. 334 No. 3 (2010), p. 682-691. These fusions are designated GLP-1-Tf and Ex-4-Tf, respectively, and were made with a non-glycosylated form of human transferrin. According to the abstract, GLP-1-Tf activated the GLP-1 receptor, was resistant to inactivation by peptidases and had a half-life of approximately 2 days. The abstract also makes it clear that the fusion proteins did not cross the blood-brain barrier, whereas, for example, the GLP-1-Tf retained the acute glucose-dependent insulin-secretory properties of native GLP-1 in diabetic animals and had a profound effect on proliferation of pancreatic beta-cells.

US 2010/0077498 A1 relates to compositions and methods for blood-brain barrier delivery in the mouse.

SUMMARY

The present invention relates to novel compounds and their use for treatment of obesity and related conditions.

In one aspect the invention relates to a construct comprising a compound targeting areas in the brain involved in the regulation of body weight and an allosteric ligand to a receptor located in the blood-brain barrier (BBB), as well as pharmaceutically acceptable salts, amides or esters thereof.

In other aspects the invention relates to a composition comprising such construct and at least one pharmaceutically acceptable excipient, the construct for use as a medicament in general and specifically in the prevention or treatment of obesity and related conditions.

In one aspect, the construct of the invention exhibits an improved binding to areas of the brain that are involved in the regulation of body weight. The binding is in particular improved in areas that are protected by the BBB.

In one aspect the compound targeting areas in the brain involved in the regulation of body weight is a GLP-1 receptor agonist (GLP-1RA).

Thus, in one aspect, the invention serves to increase the accessibility of a systemically dosed GLP-1RA to appetite regulating areas in the brain.

Also, or alternatively, the invention serves to target additional GLP-1 receptor (GLP-1R) populations in the brain, for example those that are protected by the BBB.

In one aspect these effects on appetite and body weight are obtained while keeping the glucose homeostasis at the same level as with systemic treatment with classic GLP-1 therapy (f.ex. with GLP-1 derivatives like liraglutide and semaglutide).

Also, or alternatively, the construct of the invention increases the binding of a systemically dosed GLP-1RA to brain regions expressing the GLP-1R. This can be demonstrated, for example, by a study as described in Example 16 (see FIG. 16A).

Also, or alternatively, the construct of the invention increases the binding of a systemically dosed GLP-1RA to brain regions expressing the GLP-1R which are protected by the BBB. This can be demonstrated, for example, by a study as described in Example 16 (see FIG. 16C).

Also, or alternatively, in one aspect the construct has the effect of lowering food intake. This can, for example, be demonstrated by a study as described in Example 20, part I.

Also, or alternatively, in one aspect the construct has the effect of causing weight loss. This can be demonstrated, for example, by a study as described in Example 20, part III.

In one aspect the receptor located in the BBB is the transferrin receptor (TfR).

The TfR is highly expressed in BBB endothelium and is a carrier protein for transferrin. Transferrin is an iron-binding blood plasma glycoprotein that controls the level of free iron (Fe) in biological fluids. Transferrin is needed for the import of iron into the cell and is regulated by intracellular iron concentration. It imports iron by internalising the transferrin-iron complex through receptor-mediated endocytosis. Full transcytosis via this receptor route thus seems unlikely, and this is one of the challenges to overcome to use TfR as a delivery system.

BRIEF DESCRIPTION OF DRAWINGS

A better understanding of the features of the invention will be obtained by reference to the following detailed description and the accompanying drawings of which:

FIG. 1A shows the structure of an anti TfR-Fab (SEQ ID NO: 3), prepared as described in Example 1, FIG. 1B shows the structure of a fluorescently-labelled version of the Fab in FIG. 1A (SEQ ID NO: 3) which is used in Example 19, FIG. 2 shows the structure of a control Fab (SEQ ID NO: 5) which does not bind to the TfR, prepared as described in Example 2, FIG. 3 shows the structure of an anti TfR-Fab (SEQ ID NO: 3), prepared as described in Example 3, FIG. 4 shows the structure of a control Fab (SEQ ID NO: 5) which does not bind to the TfR, prepared as described in Example 4, FIG. 5 shows the structure of a fusion protein of a control Fab and a GLP-1 analogue (SEQ ID NO: 8), prepared as described in Example 5, FIG. 6 shows the structure of a GLP-1 anti TfR-Fab fusion protein (SEQ ID NO: 11), prepared as described in Example 6, FIG. 7 shows the structure of a GLP-1 control Fab fusion protein (SEQ ID NO: 12), prepared as described in Example 7, FIG. 17A shows the result of an acute in vivo study in lean mice, more in particular the cumulative food intake (FI) in g over a period of up to 24 hours after administration of an "active" GLP-1 anti TfR-Fab conjugate, FIG. 17B shows the result of an acute in vivo study in lean mice, more in particular the plasma exposure levels in pM measured over a period of up to 24 h after dosing of an "active" GLP-1 anti TfR-Fab conjugate, FIG. 18A shows the result of an acute in vivo study in lean mice, more in particular the cumulative food intake (FI) in g over a period of 24 hours after administration of either an "active" GLP-1 anti TfR-Fab conjugate or an "inactive" GLP-1 control-Fab conjugate, FIG. 18B shows the result of an acute in vivo study in lean mice, more in particular the plasma exposure levels in pM measured over a period of up to 24 h after dosing of either an "active" GLP-1 anti TfR-Fab conjugate or an "inactive" GLP-1 control Fab conjugate, FIG. 19A shows the result of a sub-chronical in vivo study in diet-induced obese (DIO) mice, more in particular weight loss in % measured over the treatment period of 19 days with once daily administration of either an "active" GLP-1 anti TfR-Fab conjugate or an "inactive" control Fab conjugate (for further details see Example 20, part III), and FIG. 19B shows the result of a sub-chronical in vivo study in diet-induced obese (DIO) mice, more in particular plasma exposure in pM 2 hours after dosing on the last day of the treatment period (19 days with once daily administration of either an "active" GLP-1 anti TfR-Fab conjugate or an "inactive" control Fab conjugate.

DESCRIPTION

Figure 8:
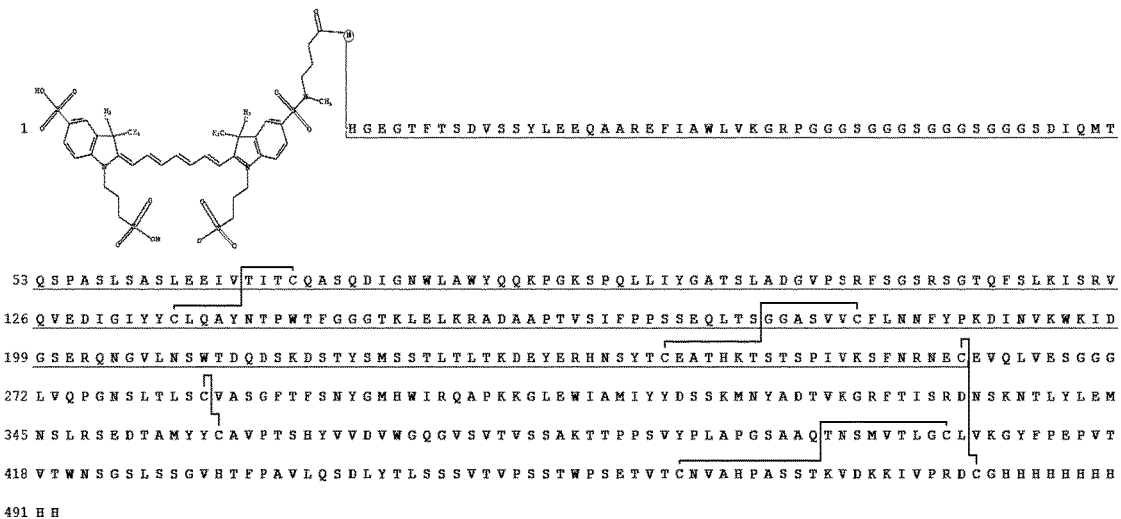
FIG. 8 shows the structure of a fluorescence labelled GLP-1 anti TfR-Fab fusion protein (SEQ ID NO: 11), prepared as described in Example 8.

In what follows, Greek letters may be represented by their symbol or the corresponding written name, for example: α=alpha; β=beta; ε=epsilon; γ=gamma; δ=delta; ω=omega; etc. Also, the Greek letter of μ may be represented by "u", e.g. in μl=ul, or in μM=uM.

In what follows chemical terminology is as usual in the art, for example the designation —C(O)— refers to a di-radical of a carbonyl group:
Chem. 7:

Chem. 7 and (COOH) as for example used in the designation —CH(COOH)— refers to a mono-radical of a carboxylic acid group of Chem. 8:

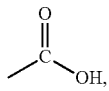

which is attached to the carbon atom shown to the left (CH).

When used herein the word "a" generally means "one or more". For example, the construct of the invention (being defined so as to comprise "a" compound targeting areas in the brain involved in the regulation of body weight and "an" allosteric ligand to a receptor located in the blood-brain barrier (BBB)) may incorporate one or more of such compounds and ligands.

Unless otherwise indicated in the specification, terms presented in singular form generally also include the plural situation.

The invention also relates to constructs, compounds, ligands, GLP-1 RA's, GLP-1 analogues, methods of preparation, compositions and uses as disclosed herein, wherein open ended terms like "comprises" and "comprising" are replaced with closed terms such as "consists of", "consisting of", and the like.

The present invention relates to novel compounds and their use for treatment of obesity and related conditions. The compounds of the invention exhibit an improved binding to areas of the brain that are involved in the regulation of body weight. The binding is in particular improved in areas that are protected by the blood-brain barrier (BBB).

In one aspect the invention relates to a construct comprising a compound targeting areas in the brain involved in the regulation of body weight and an allosteric ligand to a receptor located in the BBB, as well as pharmaceutically acceptable salts, amides or esters thereof.

Construct

The term "construct"—comprising a compound targeting areas in the brain involved in the regulation of body weight and an allosteric ligand to a receptor located in the BBB—refers to a chemical entity (molecule) in which the compound and the ligand are covalently connected, optionally via a linker.

In one embodiment the construct consists of a compound targeting areas in the brain involved in the regulation of body weight, an allosteric ligand to a receptor located in the BBB, and an optional linker.

In one embodiment the compound and the ligand are directly attached to each other (linker absent).

In another embodiment, the compound and the ligand are attached to each other via a linker.

Fusion Protein

In one embodiment, the construct is a fusion protein.

A fusion protein is a compound which can be produced by a process involving a step of recombinant expression of the entire fusion protein in a host cell.

In one embodiment, the amino acid sequence of the fusion protein consists solely of coded amino acids.

In one embodiment the protein resulting from the recombinant expression step is identical to the desired fusion protein, in which case the fusion protein is, or may be, produced by a "fully recombinant" process. In this case no further chemical modifications are needed of the fusion protein, and the expressed fusion protein can be isolated and purified and constitutes the final, desired product.

One non-limiting example of a fusion protein is the fusion protein of Example 6 (FIG. 6), in which a GLP-1 analogue is fused, via a peptidic linker (4×(GlyGlyGlySer)) (SEQ ID NO: 18), to the N-terminus of the $V_L$ domain of an anti TfR-Fab. Each of the amino acid sequences of each of these three parts consists entirely of coded amino acids.

Conjugate

In one embodiment the construct is a conjugate.

In one embodiment a "conjugate" is not a fusion protein.

In one embodiment, the covalent bonds between the compound targeting areas in the brain involved in the regulation of body weight, the allosteric ligand, and the optional linker may be formed by any chemical process, except by a fully recombinant process.

Figure 11:
FIG. 11 shows the structure of a GLP-1 anti TfR-Fab conjugate (SEQ ID NO: 3 and SEQ ID NO: 13), prepared as described in Example 11.

In one embodiment, the structural formula of the conjugate includes at least one non-coded amino acid. One non-limiting example of a non-coded amino acid is the amino acid Aib (see e.g. the conjugate of Example 11 (FIG. 11).

Also, or alternatively, the structural formula of the conjugate includes at least one element which is not an amino acid. One non-limiting example of such element is a chemical linker such as Chem. 1: —CH₂—C(O)— (see, e.g., the conjugate of Example 11 (FIG. 11) in which a linker of Chem. 1 connects the epsilon amino group of Lys 485 and the thiol group of Cys 377. Another non-limiting example of such element is a chemical linker of Chem. 2: —CH₂—C(O)-Ado-gGlu-Ado (see, e.g., the conjugate of Example 15 in which a linker of Chem. 2 connects the epsilon-amino group of Lys 438 and the thiol group of Cys 377.

In some embodiments, a conjugate can be, or is, produced by a partly recombinant process (e.g., a protein part of a desired conjugate can be, or is, produced in a recombinant expression step, and remaining part(s) of the desired conjugate can be, or are, added in one or more separate process steps, after the recombinant expression step, in one or more chemical reaction steps outside of the host cell. Such production processes may be referred to as "semi-recombinant" processes.

Areas in the Brain Involved in the Regulation of Body Weight

Non-limiting examples of areas in the brain involved in the regulation of body weight are referred to by Bloemendaal et al in "Effects of glucagon-like peptide 1 on appetite and body weight: focus on the CNS", Thematic Review, Journal of Endocrinology (2014), 221, T1-T16, see, e.g., FIG. 1 at p. T8.

Figure 16:
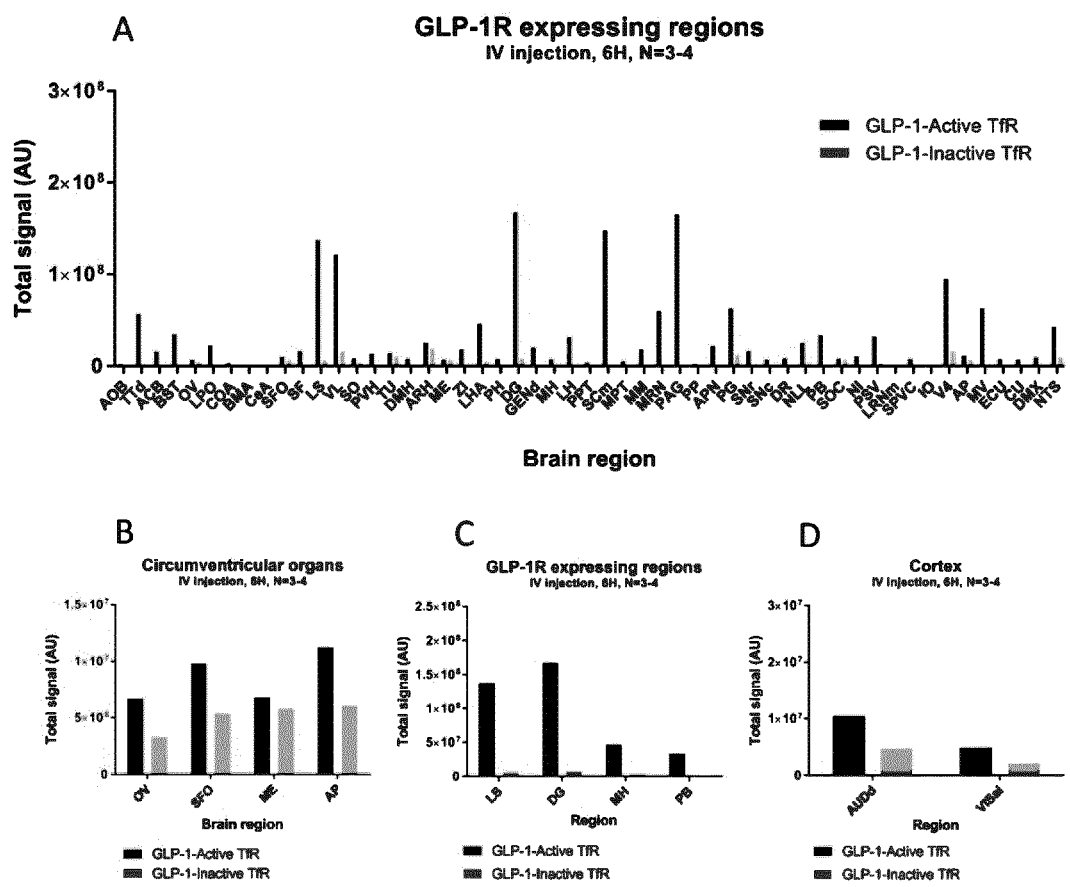
FIG. 16A shows the result of in vivo imaging of fluorescently labelled GLP-1 Fab fusion proteins after acute administration to mice, more in particular the total intensity of the fluorescence signals after quantification in all brain regions expressing the GLP-1R, for an "active" construct which binds to the TfR as well as for an "inactive" control construct that does not bind to the TfR.
FIG. 16B shows the result of in vivo imaging of fluorescently labelled GLP-1 Fab fusion proteins after acute administration to mice, more in particular the total intensity of the fluorescence signals after quantification in circumventricular organs expressing the GLP-1R but devoid of a BBB, for an "active" construct which binds to the TfR as well as for an "inactive" control construct that does not bind to the TfR.
FIG. 16C shows the result of in vivo imaging of fluorescently labelled GLP-1 Fab fusion proteins after acute administration to mice, more in particular the total intensity of the fluorescence signals after quantification in exemplary brain structures which are protected by the BBB, for an "active" construct which binds to the TfR as well as for an "inactive" control construct that does not bind to the TfR.
FIG. 16D shows the result of in vivo imaging of fluorescently labelled GLP-1 Fab fusion proteins after acute administration to mice, more in particular the total intensity of the fluorescence signals after quantification in brain regions that do not express the GLP-1R, for an "active" construct which binds to the TfR as well as for an "inactive" control construct that does not bind to the TfR.

In some embodiments, areas in the brain involved in the regulation of body weight include, without limitation, lateral septal nucleus (LS), dentate gyrus (DG), medial habenula (MH), and/or parabrachial nucleus (PB) (see FIG. 16C and Example 16).

In some embodiments, areas in the brain involved in the regulation of body weight include, without limitation, nucleus accumbens (ACB), dorsomedial nucleus of the hypothalamus (DMH), lateral hypothalamic area (LHA), and/or lateral habenula (LH).

Regulation of Body Weight

In one embodiment, regulation of body weight refers to reduction of body weight.

In one embodiment reduction of body weight may be due to one or more of the following: Reduced food intake, reduced caloric intake, reduced appetite, increased energy expenditure, and/or change in food preferences.

Thus, in some embodiments, the compound part of the construct of the invention is targeting areas in the brain involved in a) reduction of food intake, b) reduction of caloric intake, c) reduction of appetite, d) increase of energy expenditure, and/or e) change in food preferences.

In some embodiments the invention relates to a method for weight management. In some embodiments the invention relates to a method for reduction of appetite. In some embodiments the invention relates to a method for reduction of food intake.

Generally, all subjects suffering from obesity are also considered to be suffering from overweight. In some embodiments the invention relates to a method for treatment or prevention of obesity. In some embodiments the invention relates to use of the construct of the invention for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/height in meters$^2$. A human subject suffering from obesity may have a BMI of ≥30; this subject may also be referred to as obese. In some embodiments the human subject suffering from obesity may have a BMI of ≥35 or a BMI in the range of ≥30 to ≤40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the construct of the invention for treatment or prevention of overweight, optionally in the presence of at least one weight-related comorbidity. In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the construct of the invention for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

Compounds

Compounds targeting areas in the brain involved in the regulation of body weight include, without limitation, gut-derived hormones having been identified as players in the regulation of feeding by relaying meal-related information on nutritional status to the brain.

In one embodiment, the compound targeting areas in the brain involved in the regulation of body weight is a protein. In one embodiment, the compound is a polypeptide. In one embodiment, the compound is a peptide.

In one embodiment, the compound targeting areas in the brain involved in the regulation of body weight is a hormone. In one embodiment, the compound is a gut-derived hormone. In one embodiment, the hormone is selected from the group consisting of eicosanoids, steroids and amino acid/protein derivatives. In one embodiment, the hormone is an amino acid/protein derivative.

In one embodiment, the compound targeting areas in the brain involved in the regulation of body weight is a GLP-1 receptor agonist (GLP-1RA).

In one embodiment, the compound targeting areas in the brain involved in the regulation of body weight is an insulinotropic agent. This term refers to the ability to initiate a signal transduction pathway resulting in insulinotropic actions or physiological effects as is known in the art.

In one embodiment, the compound targeting areas in the brain involved in the regulation of body weight is targeting pathways in the brain involved in the regulation of body weight. In one embodiment, the compound is targeting receptors in the brain involved in the regulation of body weight.

Receptor Located in the BBB

A receptor located in the blood-brain barrier (BBB) is an endogenous receptor expressed at the brain capillary endothelium.

In one embodiment, the receptor located in the BBB is the transferrin receptor (TfR).

Allosteric/Orthosteric

An "orthosteric ligand" of a receptor is an endogenous, or primary, ligand which modulates the activation of the receptor. The site at which an orthosteric ligand binds to the receptor is designated an "orthosteric site" of the receptor.

An "allosteric ligand" of a receptor refers to a ligand that binds at a different site from that of the endogenous (orthosteric) ligand, viz. to an "allosteric site" of the receptor.

As an example, transferrin (Tf) is the orthosteric ligand which modulates the activation of the transferrin receptor (TfR), and Tf binds to an orthosteric site of the TfR. An allosteric ligand of the TfR binds at a different site from that of the orthosteric ligand (Tf), viz. to an allosteric site of the TfR.

GLP-1 Receptor Agonist

A receptor agonist may be defined as a compound that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, a "GLP-1 receptor agonist" (GLP-1RA) may be defined as a compound which is capable of binding to the GLP-1 receptor (GLP-1R) and capable of activating it. And a "full" GLP-1RA may be defined as a GLP-1 receptor agonist which is capable of eliciting a magnitude of GLP-1 receptor response that is similar to native GLP-1. In one embodiment the GLP-1 receptor is the human GLP-1 receptor.

The capability of activating the human GLP-1 receptor may suitably be determined in a medium containing membranes expressing the human GLP-1 receptor, and/or in an assay with whole cells expressing the human GLP-1 receptor.

For example, purified plasma membranes from a stable transfected cell line expressing the human GLP-1 receptor may be stimulated with the compound in question, and the potency of cAMP production measured, e.g. based on competition between endogenously formed cAMP and exogenously added biotin-labelled cAMP, which may be captured using a specific antibody.

Also, or alternatively, the response of the human GLP-1 receptor may be measured in a reporter gene assay, e.g. in a stably-transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase may be determined by adding luciferin, which by the enzyme is converted to oxyluciferin and produces bioluminescence, which is measured and is a measure of the in vitro potency. One non-limiting example of such an assay is described in Example 17.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the constructs and GLP-1RA compounds of the invention may be determined as described above, and the $EC_{50}$ of the compound or construct in question determined. The lower the $EC_{50}$ value, the better the potency.

In some embodiments, the GLP-1RA of the construct of the invention is a GLP-1 analogue. In some embodiments, the GLP-1RA of the construct of the invention is a GLP-1 derivative.

Non-limiting examples of GLP-1 analogues are those of Examples 6, 10, and 13 (FIG. 6, FIG. 10, FIG. 13), viz. amino acids 1-31 of SEQ ID NO: 11, amino acids 1-31 of SEQ ID NO: 13, and amino acids 1-31 of SEQ ID NO: 15, respectively.

A non-limiting example of a GLP-1 derivative is disclosed in Examples 10 and 13 (SEQ ID NO: 13, SEQ ID NO: 15). These are GLP-1 analogues with a covalently attached linker.

Linker

The construct of the invention may include a linker which connects the compound targeting areas in the brain involved in the regulation of body weight with the allosteric ligand to a receptor located in the BBB. The linker is in other words optional.

In one embodiment the linker is peptidic. A peptidic linker is composed of amino acids. In one embodiment the peptidic linker consists of amino acids. In one embodiment the linker consists of coded amino acids.

Non-limiting examples of peptidic linkers are: GQAPGQAPGQAPGQAPGQAPK (SEQ ID NO: 13) and GGGSGGGSGGGSGGGS (SEQ ID NO: 18) (residues 32-47 of SEQ ID NO: 11), see Examples 11 and 6 (FIG. 11 and FIG. 6, respectively)).

In another embodiment the linker is non-peptidic, or chemical. While a non-peptidic linker may include amino acid residues it does not consist entirely of amino acids.

Figure 15:
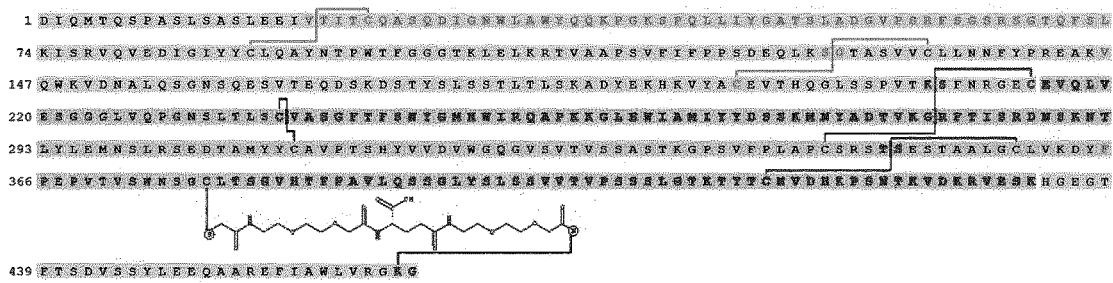
FIG. 15 shows the structure of a GLP-1 anti TfR-Fab conjugate (SEQ ID NO: 3 and SEQ ID NO: 15 modified by connecting the distal Ado of the linker of Chem. 5 (-Ado-gGlu-Ado-) to the thiol group of Cys 377 via Chem. 1 (—CH$_2$—C(O)—)), prepared as described in Example 15.

Non-limiting examples of non-peptidic linkers are: Chem. 1: —$CH_2$—C(O)—, see Example 11 (FIG. 11), and Chem. 2: —$CH_2$—C(O)-Ado-gGlu-Ado-, where Ado is a di-radical of 8-amino-3,6-dioxaoctanoic acid, Chem. 3: —NH—($CH_2$)$_2$ —O—($CH_2$)$_2$—O—$CH_2$—C(O)—, and gGlu is a di-radical of L-gamma-glutamic acid, Chem. 4: —NH—CH (COOH)—($CH_2$)$_2$—C(O)—, see Example 15 (FIG. 15).

Amino Acid, Peptide, Protein

An amino acid may be defined as a compound which comprises an amine group and a carboxylic acid group, and optionally one or more additional groups often referred to as a side chain. The amine group may, e.g., be a primary or secondary amino group. Proline is one non-limiting example of an amino acid comprising a secondary amino group.

A sub-group of amino acids are the α-amino acids where the nitrogen atom of the primary or secondary amino group is bonded to the α-carbon atom.

An amino acid residue is a radical of an amino acid as incorporated into a peptide or protein.

Peptides are distinguished from polypeptides and proteins on the basis of size. In the present context, unless otherwise specified, a peptide consists of up to and including 50 amino acid residues, whereas a polypeptide and a protein consists of more than 50 amino acid residues. A protein may consist of one or more polypeptide chains that may be arranged in a biologically functional way. In particular embodiments, the peptide consists of (i) at least 2 amino acid residues, (ii) at least 5 amino acid residues, (iii) at least 10 amino acid residues, (iv) at least 20 amino acid residues, (v) at least 30 amino acid residues, or (vi) at least 40 amino acid residues. In further particular embodiments, the polypeptide consists of (i) no more than 2000 amino acid residues, (ii) no more than 1500 amino acid residues, (iii) no more than 1000 amino acid residues, or (iv) no more than 600 amino acid residues. In still further particular embodiments, the protein consists of (i) no more than 2000 amino acid residues, (ii) no more than 1500 amino acid residues, (iii) no more than 1000 amino acid residues, (iv) no more than 600 amino acid residues, or (v) no more than 500 amino acid residues.

Amino acids may be classified based on origin, as coded amino acids or non-coded amino acids. The term "coded" amino acids (sometimes also referred to as "natural" amino acids) may be defined by reference to IUPAC (Table 1 in section 3AA-1): (www.chem.qmul.ac.uk/iupac/AminoAcid/AA1n2.html#AA1), which gives structure, trivial name, systematic name, one- and three-letter symbols for these 20 amino acids. These are all α-amino acids.

One non-limiting example of a non-coded amino acid is Aib, also known as α-aminoisobutyric acid and with the following structure:

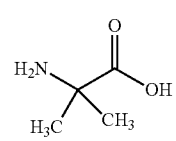

Chem. 6

GLP-1 Peptides and Analogues

The term "GLP-1 peptide" as used herein refers to the human Glucagon-Like Peptide-1 (GLP-1(7-37)), the sequence of which is included in the sequence listing as SEQ ID NO: 16, or an analogue thereof. The peptide having the sequence of SEQ ID NO: 16 may also be designated "native" GLP-1.

The term "GLP-1 analogue" or "analogue of GLP-1" as used herein refers to a peptide, or a compound, which is a variant of GLP-1(7-37) (SEQ ID NO: 16).

In the sequence listing, the first amino acid residue of SEQ ID NO: 16 (histidine) is assigned no. 1. However, in what follows, according to established practice in the art, this histidine residue is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37.

GLP-1 analogues of the constructs and derivatives of the invention may be described by reference to i) the number of the amino acid residue in native GLP-1(7-37) which corresponds to the amino acid residue which is changed (i.e., the corresponding position in native GLP-1), and to ii) the actual change.

In other words, a GLP-1 analogue is a GLP-1(7-37) peptide in which a number of amino acid residues have been changed when compared to native GLP-1(7-37) (SEQ ID NO: 16). These changes may represent, independently, one or more amino acid substitutions, additions, and/or deletions.

As is apparent from the above examples, amino acid residues may be identified by their full name, their one-letter code, and/or their three-letter code. These three ways are fully equivalent.

The expressions "a position equivalent to" or "corresponding position" may be used to characterise the site of change in a variant GLP-1(7-37) sequence by reference to native GLP-1(7-37) (SEQ ID NO: 16). Equivalent or corresponding positions, as well as the number of changes, are easily deduced, e.g. by simple handwriting and eyeballing; and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

The term "peptide", as e.g. used in the context of the GLP-1 analogues of the derivatives of the invention, refers to a compound which comprises a series of amino acids interconnected by amide (or peptide) bonds.

The GLP-1 peptides of the invention comprise at least five constituent amino acids connected by peptide bonds. In particular embodiments the GLP-1 peptide comprises at least 10, preferably at least 15, more preferably at least 20, even more preferably at least 25, or most preferably at least 28 amino acids.

In additional particular embodiments, the peptide is a) composed of, or b) consists of, i) 29, ii) 30, iii) 31, or iv) 32 amino acids.

In a still further particular embodiment the peptide consists of amino acids interconnected by peptide bonds.

In what follows, all amino acids of the GLP-1 peptide for which the optical isomer is not stated is to be understood to mean the L-isomer (unless otherwise specified).

Pharmaceutically Acceptable Salt, Amide Ester

The construct of the invention may be in the form of a pharmaceutically acceptable salt, amide, or ester. This is also the case for its constituent compound and ligand parts as such.

Salts are e.g. formed by a chemical reaction between a base and an acid, e.g.: $2NH_3+H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts may be formed with added cations or anions between anionic or cationic groups, respectively. These groups may be situated in the compound part, in the ligand part, and/or in the optional linker part of the constructs of the invention.

Non-limiting examples of anionic groups of the constructs of the invention include free carboxylic groups, e.g. a free carboxylic acid group at a C-terminal amino acid of the construct, and free carboxylic groups at internal acid amino acid residues such as Asp and Glu.

Non-limiting examples of cationic groups include a free amino group at the N-terminus, if present, as well as any free amino group of internal basic amino acid residues such as His, Arg, and Lys.

The ester of the construct of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus, and/or any free carboxylic group internally in the construct.

The amide of the construct of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus, any free carboxylic group internally in the construct, the free amino group at the N-terminus of the construct, and/or any free or substituted amino group internally in the construct.

In a particular embodiment, the construct is in the form of a pharmaceutically acceptable salt. In another particular embodiment, the construct is in the form of a pharmaceutically acceptable amide, preferably with an amide group at the C-terminus. In a still further particular embodiment, the construct is in the form a pharmaceutically acceptable ester.

Production Processes

The production of proteins and peptides like the control Fab's, anti TfR-Fab's and GLP-1 analogues disclosed herein is well known in the art.

GLP-1 analogues may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dorwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those constructs of the invention which include non-coded amino acids may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of constructs are included in the experimental part.

Pharmaceutical Compositions

In one embodiment, the composition of the invention is a pharmaceutical composition.

Pharmaceutical compositions comprising a construct of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19th edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

A pharmaceutical composition may comprise a buffer.

A pharmaceutical composition may comprise a preservative.

A pharmaceutical composition may comprise a chelating agent.

A pharmaceutical composition may comprise a stabiliser.

A pharmaceutical composition may comprise one or more surfactants.

A pharmaceutical composition may comprise one or more protease inhibitors.

The construct of the invention may be administered in the form of a pharmaceutical composition. It may be administered to a patient in need thereof at several sites.

The route of administration may be, for example, parenteral.

A composition may be administered in several dosage forms, for example as a solution; a suspension; an emulsion; a microemulsion; multiple emulsions; an injection solution; an infusion solution.

Systemic or parenteral administration may be performed by subcutaneous, intramuscular, intraperitoneal, or intravenous injection by means of a syringe, optionally a pen-like syringe, or by means of an infusion pump.

The treatment with a construct according to the invention may also be combined with one or more additional pharmacologically active substances.

The treatment with a construct according to the invention may also be combined with a surgery that influences the glucose levels, and/or lipid homeostasis such as gastric banding or gastric bypass.

Particular Embodiments

The invention is further described by the following non-limiting embodiments.

1. A construct comprising a compound targeting areas in the brain involved in the regulation of body weight and an allosteric ligand to a receptor located in the blood-brain barrier (BBB); or a pharmaceutically acceptable salt, amide or ester thereof.
2. The construct of embodiment 1, wherein the compound is targeting pathways in the brain involved in the regulation of body weight.
3. The construct of any of embodiments 1-2, wherein the compound is targeting receptors in the brain involved in the regulation of body weight.
4. The construct of any of embodiments 1-3, wherein the compound is a peptide, a polypeptide, or a protein.
5. The construct of any of embodiments 1-4, wherein the compound is a hormone.
6. The construct of embodiment 5, wherein the hormone is selected from the group consisting of eicosanoids, steroids and amino acid/protein derivatives.
7. The construct of embodiment 5, wherein the hormone is an amino acid/protein derivative.
8. The construct of any of embodiments 1-7, wherein the compound is a gut-derived hormone.
9. The construct of any of embodiments 1-8, wherein the compound is an insulinotropic agent.
10. The construct of any of embodiments 1-9, wherein the compound is a GLP-1 receptor agonist (GLP-1RA).
11. The construct of any of embodiments 1-10, wherein the receptor located in the BBB is the transferrin receptor (TfR).
12. The construct of embodiment 11, wherein the allosteric ligand binding to the TfR is a peptide, a polypeptide, or a protein.
13. The construct of any of embodiments 11-12, wherein the allosteric ligand binding to the TfR is an anti-transferrin receptor Fab (anti TfR-Fab).
14. The construct of any of embodiments 1-13 which is a fusion protein or a conjugate.
15. The construct of any of embodiments 1-14, which further comprises a linker.
16. The construct of embodiment 15, wherein the linker is peptidic or non-peptidic.
17. The construct of any of embodiments 1-16, which is a GLP-1RA.
18. The construct of any of embodiments 1-17, which is a full GLP-1RA. 19. The construct of any of embodiments 1-18, which has an in vitro potency corresponding to an $EC_{50}$ at or below 1000 pM, determined using the assay of Example 17.
20. The construct of any of embodiments 1-19, which is capable of binding to the GLP-1R.
21. The construct of any of embodiments 1-20, which has a GLP-1R binding affinity corresponding to an $IC_{50}$ at or below 100 nM, determined using the assay of Example 18.
22. The construct of any of embodiments 1-21, which is capable of binding to the transferrin receptor (TfR).
23. The construct of any of embodiments 1-22, which is capable of inhibiting the uptake of a TfR targeted antibody.

24. The construct of embodiment 23, which inhibits uptake of the TfR targeted antibody corresponding to an $IC_{50}$ at or below 100 nM, determined using the assay of Example 19.
25. The construct of embodiment 24, for which the $IC_{50}$ value is lower than the $IC_{50}$ value of a control construct which incorporates the same GLP-1RA but a ligand which does not bind to the TfR, wherein both $IC_{50}$ values are determined using the assay of Example 19.
26. The construct of any of embodiments 11-25, which exhibits an increased binding to brain regions expressing the GLP-1R as compared to a control construct which only differs from the construct by incorporating a ligand which does not bind to the TfR.
27. The construct of embodiment 26, wherein the binding to the brain regions expressing the GLP-1R is determined using in vivo imaging of fluorescently labelled constructs.
28. The construct of embodiment 27, which results in higher fluorescence signals as compared to a control construct in at least a majority of the brain regions expressing the GLP-1R, wherein the brain regions expressing the GLP-1R are as set out in FIG. 16A.
29. The construct of embodiment 28, wherein the fluorescence signals are higher in at least 50%, 60%, 70%, 80%, or preferably at least 90% of the GLP-1R expressing brain regions.
30. The construct of any of embodiments 26-29, wherein the binding to brain regions expressing the GLP-1R is determined essentially as described in Example 16.
31. The construct of any of embodiments 11-30, which exhibits an increased binding to GLP-1R expressing brain regions that are protected by the BBB as compared to a control construct which only differs from the construct by incorporating a ligand which does not bind to the TfR.
32. The construct of embodiment 31, which results in higher fluorescence signals as compared to a control construct in at least a majority of the BBB protected brain regions expressing the GLP-1R.
33. The construct of embodiment 32, wherein the BBB protected brain regions expressing the GLP-1R are LS, DG, MH, and PB as set out in FIG. 16C.
34. The construct of embodiment 32, wherein the BBB protected brain regions expressing the GLP-1R are ACB, DMH, LHA, and LH.
35. The construct of any of embodiments 32-34, wherein the fluorescence signals are higher in at least 50%, 60%, 70%, 80%, or at least 90% of the GLP-1R expressing brain regions.
36. The construct of any of embodiments 32-35, wherein the fluorescence signal is at least two, three, four, five, six, seven, eight, nine, or at least ten times higher than the fluorescence signal for the control construct.
37. The construct of any of embodiments 32-36, wherein the binding to GLP-1R expressing brain regions that are protected by the BBB is determined essentially as described in Example 16.
38. The construct of any of embodiments 1-37, which lowers food intake.
39. The construct of embodiment 38, which lowers food intake dose dependently.
40. The construct of any of embodiments 38-39, which causes a lower food intake as compared to a control which only differs from the construct by incorporating a ligand which does not bind to the TfR.
41. The construct of any of embodiments 38-40, wherein food intake is cumulative food intake in g over a period of 24 hours.
42. The construct of any of embodiments 38-41, wherein food intake is determined in an acute study in lean mice, essentially as described in Example 20, part I or part II.
43. The construct of any of embodiments 1-42, which causes weight loss.
44. The construct of embodiment 43, which causes a higher weight loss as compared to a control which only differs from the construct by incorporating a ligand which does not bind to the TfR.
45. The construct of any of embodiments 43-44, wherein weight loss is determined in a sub-chronical study in DIO mice, essentially as described in Example 20, part III.
46. A composition comprising a construct of any of embodiments 1-45 and at least one pharmaceutically acceptable excipient.
47. The construct of any of embodiments 1-45 or the composition of embodiment 46 for use as a medicament.
48. The construct of any of embodiments 1-45 or the composition of embodiment 46 for use in the prevention or treatment of obesity.
49. A method for the prevention or treatment of obesity, comprising administering the construct according to any of embodiments 1-45 or the composition of embodiment 46.

EXAMPLES

This experimental part starts with a list of abbreviations, and is followed by a section including general methods for detecting and characterising the constructs of the invention. Then follows a number of examples which relate to the preparation of specific construct parts and constructs, and at the end a number of examples have been included relating to the activity and properties of these analogues and derivatives (section headed pharmacological methods).

The examples serve to illustrate the invention.

LIST OF ABBREVIATIONS

Ac acetyl
ACB nucleus accumbens
ad lib ad libitum
Ado 8-amino-3,6-dioxaoctanoic acid
AOB accessory olfactory bulb
AP area postrema
APN anterior pretectal nucleus
ARH arcuate hypothalamic nucleus
AU arbitrary unit
AUC area under the curve
BBB blood-brain barrier
BBB-R blood-brain barrier receptor
BGG bovine gamma globulin
BHK baby hamster kidney
BMA basomedial amygdalar nucleus
BID bis in die (twice daily)
Boc t-butyloxycarbonyl
BrAc bromo acetamide
BST bed nuclei of the stria terminalis
cAMP cyclic AMP
CeA central amygdalar nucleus
$C_H$ constant region heavy chain CHO Chinese hamster ovary
$C_L$ constant region light chain
CLND chemiluminescent nitrogen detection
CNS central nervous system
COA cortical amygdalar area
CRE cAMP response element
CU cuneate nucleus
CV coefficient of variation
Da Dalton
DAPI 4',6-diamidino-2-phenylindole
DBE dibenzyl ether
DCM dichloromethane
DF diafiltration
DG dentate gyrus
$dH_2O$ demineralised water
DIC diisopropylcarbodiimide
DIO diet-induced obese
DMEM dulbecco modified eagle medium
DMF dimethylformamide
DMH dorsomedial nucleus of the hypothalamus
DMSO dimethyl sulfoxide
DMX dorsal motor nucleus of the vagus nerve
DPP-4 dipeptidyl peptidase 4
DR dorsal nucleus raphe
ECU external cuneate nucleus
EDTA ethylenediaminetetraacetic acid
Fab fragment antigen-binding (antigen-binding fragment)
FI food intake
Fmoc 9-fluorenylmethyloxycarbonyl
G418 geneticin
GENd geniculate group, dorsal thalamus
gGlu glutamic acid for incorporation/when attached to another molecule via an amide bond involving the carboxylic acid group at the gamma position of the side chain of Glu
GLP-1 glucagon like peptide-1
GLP-1R glucagon like peptide-1 receptor
GLP-1RA glucagon like peptide-1 receptor agonist
H hours
HBSS Hanks' balanced salt solution
HEK human embryonic kidney
HEPES 4-(2-hydroxyethyl)-1-piperazineethanesulfonic acid
HFIP 1,1,1,3,3,3-hexafluoro-2-propanol or hexafluoroisopropanol
HPLC high performance liquid chromatography
HSA human serum albumin
IgG4 subclass four of immunoglobulin G
IO inferior olivary complex
i.v. intravenous
L liter
LCMS liquid chromatography mass spectroscopy
LH lateral habenula
LHA lateral hypothalamic area
lib libitum
LOCI luminescence oxygen channeling immunoassay
LoQ lower limit of quantification
LPO lateral preoptic area
LRNm lateral reticular nucleus, magnocellular
LS lateral septal nucleus
LSFM light sheet fluorescence microscopy
ME median eminence
MH medial habenula
MM medial mammillary nucleus
MPT medial pretectal area
MQ de-ionised water
dRN midbrain reticular nucleus
Mtt 4-methyltrityl
MV medial vestibular nucleus
NaP sodium phosphate
NBF neutral buffered formalin
NI nucleus incertus
NLL nucleus of the lateral lemniscus
NTS nucleus of the solitary tract
OEG same as Ado
O/N overnight
OtBu tert butyl ester
OV vascular organ of the lamina terminalis
Oxyma Pure® cyano-hydroxyimino-acetic acid ethyl ester
PB parabrachial nucleus
Pbf 2,2,4,6,7-pentamethyldihydrobenzofuran-5-sulfonyl
PBS phosphate buffered saline
Pen/strep Penicillin Streptomycin
PFA paraformaldehyde
QC quality control
QD quaque die (once daily)
QW quaque (once weekly)
Rt retention time
RT room temperature
s.c. sub cutaneous
SDS-PAGE sodium dodecyl sulfate polyacrylamide gel electrophoresis
SEM standard error of mean
SEC-HPLC size exclusion high performance liquid chromatography
SFO subfornical organ
SPPS solid phase peptide synthesis
tBu tert. butyl
TCEP tris(2-carboxyethyl)phosphine
TEA triethanolamine
Tf transferrin
TFA trifluoroacetic acid
TfR transferrin receptor
TFT tangential flow filtration
THF tetrahydrofuran
TIC total ion count
TIPS triisopropylsilane
TNP 2,4,6-trinitrophenol
Tris tris(hydroxymethyl)aminomethane or 2-amino-2-hydroxymethyl-propane-1,3-diol
Trt triphenylmethyl (trityl)
Tween20 polyethylene glycol sorbitan monolaurate
UF ultrafiltration
ULoQ upper limit of quantification
$V_L$ light chain variable domain
WGA wheat germ agglutinin
General Methods of Detection and Characterisation
1. LC-MS Methods
Method: LCMS_34

| | |
|---|---|
| System | LC-system: Waters Acquity UPLC H Class |
| | Column:: Waters Acquity BEH, C-18, 1.7 m, 2.1 mm × 50 mm |
| | Detector:: Waters Xevo G2-XS QTof |
| Detector setup | Ionisation method: ES |
| | Scanning range: 50-4000 amu |
| | Operating mode: MS resolution mode positive/ne: positive mode |
| | Voltage: Capillary 3.00 kV |
| | Sample cone 40 V |
| | Source 80 V |
| | Temperature: Source 150 C. |
| | Desolvation 500 C. |
| | Scantime 0.500 s |
| | Interscandelay: 0.014 s |

-continued

| | |
|---|---|
| Conditions | Linear gradient: 5% to 95% B<br>Gradient run-time: 4.0 minutes<br>Total run-time: 7.0 minutes<br>Flow rate: 0.4 ml/min<br>Column temperature: 40 C. |
| Eluents | Solvent A: 99,90% MQ-water, 0.1% formic acid<br>Solvent B: 99.90% acetonitrile, 0.1% formic acid<br>Solvent C: 99.90% MQ water 0.1% TFA<br>Gradient: A 90-0%<br>　　　　　B 5-95%<br>　　　　　C 5% |
| Results to upload | Mass calc; Mass found (m1/z; m2/z;<br>Rt = xx, x min |
| Results specification and validation | Mass found is the mass found of the compound<br>M/z found is the molecular ion found<br>((M + z)/z) of the compound<br>Calculated Mass is the molecular weight of the desired compound<br>Calculated M/z is the molecular weight (M + z)/z of the desired compound<br>Purity: Total ion current (TIC) AUC of analyte peak, in percent of total AUC excl solvent peak, as reported by system software. Identity: Mass of each analyte mass peak expressed as m/z from highest to lowest. Scanning range is the range scanned in the method used. Detection method is e.g linear reflector |

Method: LCMS_36
This protocol outlines the MS method depicted by the protocol title, and is used to link the method description to the results of the analysis. The method is used to measure the purity of the analyte by a chromatographic separation of the sample, and to identify and quantify the components by their mass spectra and total ion count (TIC)
LC-system: Waters Acquity UPLC H Class. Step gradient: 5% to 25% B 1 min 25-65%

| | |
|---|---|
| B 6 min System | LC-system: Waters Acquity UPLC H Class<br>Column: Waters Acquity BEH, C-18, 1.7 μm, 2.1 mm × 50 mm<br>Detector: Waters Xevo G2-XS QTof |
| Detector setup | Ionisation method: ES<br>Scanning range: 50-4000 amu<br>Operating mode: MS resolution mode<br>positive/ne: positive mode<br>Voltage: Capillary 3.00 kV<br>　　　　　Sample cone 80 V<br>　　　　　Source 60 V<br>Temperature: Source 150° C.<br>　　　　　　Desolvation 500° C.<br>Scantime: 0.500 s<br>Interscandelay: 0.014 s |
| Conditions | Linear gradient: 5% to 95% B<br>Gradient run-time: 4.0 minutes<br>Total run-time: 7.0 minutes<br>Flow rate: 0.4 ml/min<br>Column temperature: 40° C. |
| Eluents | Solvent A: 99, 90% MQ-water, 0.1% formic acid<br>Solvent B: 99.90% acetonitrile, 0.1% formic acid<br>Solvent C: 99.99% MQ water 0.01% TFA<br>Gradient: A 90-70% 1 min 70-30% 6 min,<br>　　　　　　30-0% 0.5 min 0% 0.5 min<br>　　　　　　B 5-25% 1 min 25-65% 6 min<br>　　　　　　65-95% 0.5 min 95% 0.5 min<br>　　　　　　C 5% |
| Results to upload | Mass calc; Mass found (m1/z; m2/z; . . .<br>Rt = xx, x min |
| Results specification and validation | Mass found is the mass found of the compound<br>M/z found is the molecular ion found<br>((M + z)/z) of the compound<br>Calculated Mass is the molecular weight of the desired compound<br>Calculated M/z is the molecular weight (M + z)/z of the desired compound LC)<br>Purity: Total ion current (TIC) AUC of analyte peak, in percent of total AUC excl solvent peak, as reported by system software. Identity: Mass of each analyte mass peak expressed as m/z from highest to lowest. Scanning range is the range scanned in the method used. Detection method is e.g linear reflector |

Example 1

Transient Expression of Anti TfR-Fab

This example describes the transient expression of the anti Tfr-Fab shown in FIG. 1A (SEQ ID NO: 3).

```
Light chain (SEQ ID NO: 1):
DIQMTQSPASLSASLEEIVTITCQASQDIGNWLAWYQQKPGKSPQLL

IYGATSLADGVPSRFSGSRSGTQFSLKISRVQVEDIGIYYCLQAYNT

PWTFGGGTKLELKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

Heavy chain (SEQ ID NO: 2):
EVQLVESGGGLVQPGNSLTLSCVASGFTFSNYGMHWIRQAPKKGLEW

IAMIYYDSSKMNYADTVKGRFTISRDNSKNTLYLEMNSLRSEDTAMY

YCAVPTSHYVVDVWGQGVSVTVSSASTKGPSVFPLAPCSRSTSESTA

ALGCLVKDYFPEPVTVSWNSGCLTSGVHTFPAVLQSSGLYSLSSVVT

VPSSSLGTKTYTCNVDHKPSNTKVDKRVESK
```

The anti TfR-Fab was designed as a chimeric Fab with variable domains as published in US 2010/0077498 A1, and human $C_L$ and IgG4 $C_H1$ domains. The $C_H1$ domain carries an A158C mutation to generate a cysteine handle for chemical conjugation.

Nucleic acid sequences encoding the anti TfR-Fab were cloned into a pTT5-derived expression vector. To express the Fab, HEK293 6E cells were cultured to the cell density of 1×10E6 cells/ml and transfected with the expression vector plasmid DNA using lipofectin (Invitrogen, cat. no. 12347-500). The expression supernatant was harvested by centrifugation and filtering of the cell culture 5 days after the transfection.

The cell culture supernatant containing secreted anti TfR-Fab was applied to a protein G Sepharose 4FF affinity column (GE Healthcare) equilibrated in phosphate buffered saline (PBS). The bound Fab was eluted with 0.1 M glycine-HCl, pH 2.8. Fractions were collected and neutralized immediately with 1/20 volume 2 M Tris-HCl, pH 9.0. The pooled fractions were then diluted into 25 mM NaOAc pH 5.0 and applied to a SP HP column (GE Healthcare). The bound Fab was eluted with a 100-400 mM linear gradient of NaCl in 25 mM NaOAc pH 5.0 and buffer-exchanged to PBS on a G25 desalting column (GE Healthcare). Purified protein was sterilized by filtration through a 0.2 mm filter unit (Sartorius). The purity of anti TfR-Fab was analysed by SDS-PAGE and size-exclusion HPLC. The Fab identity was confirmed by mass spectrometry.

The purity was above 95% by SDS-PAGE and 99.1% by SEC-HPLC (A280 nm). The observed mass was 47198.3 Da, which is consistent with the theoretical mass (47198.5 Da).

Example 2

Transient Expression of Control Fab

This example describes the transient expression of a control Fab shown in FIG. 2, which does not bind to the TfR. The control Fab of FIG. 2 has the amino acid sequence of SEQ ID NO: 5.

```
Light chain (SEQ ID NO: 4):
DIVMTQTPLSLSVTPGQPASISCRSSQSLLHSNGNTYLHWYLQKPGQS

PQLLIYKVSNRFSGVPDRFSGSGSGTDFTLKISRVEAEDVGVYYCSQS

THVPWTFGQGTKVEIKRTVAAPSVFIFPPSDEQLKSGTASVVCLLNNF

YPREAKVQWKVDNALQSGNSQESVTEQDSKDSTYSLSSTLTLSKADYE

KHKVYACEVTHQGLSSPVTKSFNRGEC
```

A control Fab was designed to be with the variable domains of the light chain of anti-TNP antibody (SEQ ID NO: 4) and the same heavy chain as in the anti-TfR antibody of Example 1 (SEQ ID NO: 2).

A similar procedure as described in Example 1 was used to clone and express the control Fab.

The purity was above 95% by SDS-PAGE and 99.2% by SEC-HPLC (A280 nm). The observed mass was 47787.4 Da, which is consistent with the theoretical mass (47787.0 Da).

Example 3

Generation of a Stable Cell Line Expressing Anti TfR-Fab

This example describes the generation of a stable cell line expressing the anti TfR-Fab shown in FIG. 3 (same as shown in FIG. 1A, SEQ ID NO: 3).

A stable cell line expressing the anti TfR-Fab of Example 1 was generated using a CHO K1SV GS KO cell line with GS selection (Lonza). The Fab light chain (SEQ ID NO: 1) and heavy chain (SEQ ID NO: 2) with an N terminal CD33 signal peptide (SEQ ID NO: 17) were subcloned into a pEE17.4 vector (Lonza). The DNA was linearized and transfected into CHO K1SV GS KO cell lines by electroporation. The transfected cell micropools were propagated in CD CHO medium (Thermo Fisher Scientific) with a MSX (Sigma-Aldrich) concentration of 25 μM for two weeks. The cells were then transferred to 96 deep well plates without MSX and the highest expressing 24 micropools were selected by Fortebio analysis using protein G sensor (Fortebio).

To achieve higher expression stability, single cell clones were isolated with the selected high expressing micropools by limited dilutions. The cells were grown for 2-3 weeks and 96 single clones were picked and screened by Fortebio. The top 24 clones were further propagated in 24 well plates and ranked by Fortebio with protein G sensor and SDS PAGE analysis. Six highest expressing cell clones each were used for further stability test. Cells before and after 30 days propagation were cultured in Fed-batch culture for the expression level evaluation by HPLC (Fed-batch culture is a 12 day culture with two nutrient feeds on day 3 and day 7). Two single clones were stable with expression levels after 30 days' passage of above 70%.

The stable cell lines expressing the Fabs were revived and propagated. The cell culture was then inoculated into a 13 L Sartorius bioreactor with the initial volume of 10.5 L in CD-CHO medium and the cell density to be 0.3×10E6 cells/ml. The fed-batch cell culture was maintained at 36.5° C., Dissolved Oxygen level of 40%, and pH of 7 (±0.3). Nutrient feeding was made based on the cell density and glucose level. The cell culture was harvested after 13 days using Millipore depth-filter MD0HC054H1.

The anti-TfR Fab was purified, sterilised, and analysed as described in Example 1.

The purity was above 95% by SDS-PAGE and 96.7% by SEC-HPLC (A280 nm). The observed mass was 47199.3 Da, which is consistent with the theoretical mass (47198.5 Da).

Example 4

Generation of a Stable Cell Line Expressing Control Fab

This example describes the generation of a stable cell line expressing the control Fab shown in FIG. 4 (same as shown in FIG. 2, SEQ ID NO: 5).

A stable cell line expressing the control Fab of Example 2 was generated as described in Example 3, except that the Fab light chain of SEQ ID NO: 4 was used instead of that of SEQ ID NO: 1. Also the measures to achieve higher expression stability described in Example 3 were followed. Three single clones were stable with expression levels above 70% after 30 days' passage.

The stable cell lines expressing the control Fabs were further cultivated in a 13 L Sartorius bioreactor as described in Example 3.

The cell culture supernatant containing secreted control Fab was concentrated and buffer exchanged to 25 mM NaOAc pH 5.0 using ultrafiltration/diafiltration (UF/DF) in tangential flow filtration (TFF) system (Millipore), then applied to a SP HP column (GE Healthcare). The bound Fab was eluted with a 0-350 mM linear gradient of NaCl in 25 mM NaOAc pH 5.0 and buffer-exchanged to PBS using UF/DF in TFF system (Millipore).

Purified control Fab was sterilized by filtration through a 0.2 mm filter unit (Sartorius). The purity was analysed by SDS-PAGE and size-exclusion HPLC. The Fab identity was confirmed by mass spectrometry.

The purity was above 95% by SDS-PAGE and 98.7% by SEC-HPLC (A280 nm). The observed mass was 47787.5 Da, which is consistent with the theoretical mass (47787.0 Da).

Example 5

Transient Expression of GLP-1 Anti TNP-Fab Fusion Protein

This example describes the expression of a fusion protein shown in FIG. 5 (SEQ ID NO: 8) of a control Fab and a GLP-1 analogue. The control Fab is an anti-TNP Fab, where TNP refers to 2,4,6-trinitrophenol.

```
Light chain (SEQ ID NO: 6):
HGEGTFTSDVSSYLEEQAAREFIAWLVKGRPGGGSGGGSGGGSGGGS

DIVMTQTPLSLSVTPGQPASISCRSSQSLLHSNGNTYLHWYLQKPGQ

SPQLLIYKVSNRFSGVPDRFSGSGSGTDFTLKISRVEAEDVGVYYCS

QSTHVPWTFGQGTKVEIKRTVAAPSVFIFPPSDEQLKSGTASVVCLL
```

-continued
NNFYPREAKVQWKVDNALQSGNSQESVTEQDSKDSTYSLSSTLTLSK

ADYEKHKVYACEVTHQGLSSPVTKSFNRGE
C

Heavy chain (SEQ ID NO: 7):
QVQLQESGPGLVKPSETLSLTCTVSGGSISSGYWNWIRQPPGKGLEW

IGTISYSGDTYYNPSLKSRVTISVDTSKNQFSLKLSSVTAADTAVYY

CARYGSYVFDYWGQGTTVTVSSASTKGPSVFPLAPCSRSTSESTAAL

GCLVKDYFPEPVTVSWNSGALTSGVHTFPAVLQSSGLYSLSSVVTVP

SSSLGTKTYTCNVDHKPSNTKVDKRVESKHHHHHHHHHH

The two chain Fab fusion protein is comprised of a light chain (SEQ ID NO: 6) and a heavy chain (SEQ ID NO: 7). In the light chain an active GLP-1 analogue is fused through a flexible 4×(GlyGlyGlySer) (SEQ ID NO: 18) linker, to the N-terminus of the $V_L$ domain of the anti TNP-Fab of Example 2 (SEQ ID NO: 4). In the heavy chain the C-terminus of the $C_H1$ domain is extended to include a e decahistidine purification tag. Thus, the light chain may be referred to as "GLP-1-(GGGS)$_4$-aTNP light chain" (SEQ ID NO: 18) and the heavy chain as "aTNP decahistidine heavy chain".

Nucleic acid sequences encoding the anti TNP-Fab fusion were cloned into a pTT-derived expression vector as described in Example 1.

To express the fusion protein, Expi293F cells (ThermoFisher Scientific, cat. no. A14527) were grown in suspension culture in Expi293 Expression™ medium (ThermoFisher Scientific, cat. no. A1435101) to a cell density of 3×10E6 cells/ml. Transient transfection was performed with a mix of ExpiFectamine™ 293 Reagent (ExpiFectamine™ 293 Transfection Kit, ThermoFisher Scientific, cat. no. A14525) and plasmid DNA encoding the two protein chains. Transfection Enhancers 1 and 2 from the ExpiFectamine™ 293 Transfection Kit were added the day after transfection. The expression was harvested by centrifugation and filtering of the cell culture 4 days after the transfection.

The cell culture supernatant containing secreted GLP-1 anti TNP-Fab fusion protein was applied to 2×5 ml HisTrap Excel columns (GE Healthcare) equilibrated in 50 mM NaP (sodium phosphate), 300 mM NaCl, 10 mM Imidazole pH 7.5. The bound fusion protein was eluted with 50 mM NaP, 300 mM NaCl, 500 mM Imidazole pH 7.5. Fractions were pooled and applied to a Superdex 200 16_600 column (GE Healthcare) equilibrated in PBS. The purified protein was sterilized by filtration through a 0.2 μm filter unit. The purity of the fusion protein was analysed by non-reducing SDS-PAGE and produced a single band indicating >90% purity and size-exclusion HPLC showed 12% high molecular weight species. The fusion protein identity was confirmed by mass spectrometry. The measured intact average mass 52977 Da and peptide mass mapping of tryptic peptides (data not shown) showed that the N-terminal glutamic acid on the $V_H1$ domain (SEQ ID NO: 7) was in fact a pyroglutamic acid in the purified protein.

Example 6

Transient Expression of GLP-1 Anti TfR-Fab Fusion Protein

This example describes the expression of a fusion protein shown in FIG. 6 (SEQ ID NO: 11) of an anti TfR-Fab and a GLP-1 analogue.

Light chain (SEQ ID NO: 9):
HGEGTFTSDVSSYLEEQAAREFIAWLVKGRPGGGSGGGSGGGSGGGS

-continued
DIQMTQSPASLSASLEEIVTITCQASQDIGNWLAWYQQKPGKSPQLL

IYGATSLADGVPSRFSGSRSGTQFSLKISRVQVEDIGIYYCLQAYNT

PWTFGGGTKLELKRADAAPTVSIFPPSSEQLTSGGASVVCFLNNFYP

KDINVKWKIDGSERQNGVLNSWTDQDSKDSTYSMSSTLTLTKDEYER

HNSYTCEATHKTSTSPIVKSFNRNEC

Heavy chain (SEQ ID NO: 10):
EVQLVESGGGLVQPGNSLTLSCVASGFTFSNYGMHWIRQAPKKGLEW

IAMIYYDSSKMNYADTVKGRFTISRDNSKNTLYLEMNSLRSEDTAMY

YCAVPTSHYVVDVWGQGVSVTVSSAKTTPPSVYPLAPGSAAQTNSMV

TLGCLVKGYFPEPVTVTWNSGSLSSGVHTFPAVLQSDLYTLSSSVTV

PSSTWPSETVTCNVAHPASSTKVDKKIVPRDCGHHHHHHHHHH

The two chain Fab fusion protein is comprised of a light chain (SEQ ID NO: 9) and a heavy chain (SEQ ID NO: 10). In the light chain an active GLP-1 analogue is fused through a flexible 4×(GlyGlyGlySer) (SEQ ID NO: 18) linker to the N-terminus of the $V_L$ domain of an anti TfR-Fab. In the heavy chain the C-terminus of the $C_H1$ Fab domain is extended to include a decahistidine purification tag. Thus, the light chain may be referred to as "GLP-1-(GGGS)$_4$-aTfR light chain" (SEQ ID NO: 18) and the heavy chain as "aTfR-decahistidine heavy chain".

Nucleic acid sequences encoding the anti TfR-Fab fusion were cloned into a pTT-derived expression vector as described in Example 1.

The fusion protein was expressed in expi293F cells and the supernatant harvested as described in Example 5.

The cell culture supernatant containing secreted GLP-1 anti TfR-Fab fusion protein was applied to 2×5 ml HisTrap Excel columns (GE Healthcare) and further purified and sterilised as described in Example 5 with the addition of a stringency wash with 50 mM NaP (sodium phosphate), 300 mM NaCl, 30 mM Imidazole pH 7.5 before elution from the HisTrap Excel columns.

The purity of the fusion protein was analysed by SDS-PAGE and size-exclusion HPLC showing greater than 95% purity. The fusion protein identity was confirmed by mass spectrometry. The average intact mass was measured to be 53243.7 Da by mass spectrometry, thereby confirming the identity of the purified protein.

Example 7

Transient Expression of GLP-1 Control Fab Fusion Protein

This example describes the expression of a fusion protein shown in FIG. 7 (SEQ ID NO: 12) of another control Fab and a GLP-1 analogue.

The plasmid DNA encoding the light chain (SEQ ID NO: 6), of this this protein is the same as used in Example 5 and the plasmid DNA encoding the heavy chain (SEQ ID NO: 10) of this protein is the same as used in Example 6. This leads to a hybrid construct with no TfR binding albeit still with an active GLP-1 element similar to the GLP-1 anti-TfR Fab of Example 6 (SEQ ID NO: 11).

Nucleic acid sequences encoding the control Fab fusion were cloned into a pTT-derived expression vector as described in Example 1.

The fusion protein was expressed in expi293F cells and the supernatant harvested as described in Example 5.

The cell culture supernatant containing secreted fusion protein was applied to 2×5 ml HisTrap Excel columns (GE Healthcare) and further purified and sterilised as described in Example 5.

The purity of the Fab fusion protein was analysed by SDS-PAGE and size-exclusion HPLC showing greater than 95% purity. The fusion protein identity was confirmed by mass spectrometry. The average intact mass was measured to be 53662.9 Da by mass spectrometry, thereby confirming the identity of the purified protein.

Example 8

Preparation of Fluorescence Labelled GLP-1 Anti TfR-Fab Fusion Protein

This example describes the fluorescence labelling of the GLP-1 anti TfR-Fab fusion protein of Example 6 (SEQ ID NO: 11). The fluorescence labelled compound is shown in FIG. 8 (please note that the labelling is randomly attached and not just on the N-terminal as depicted).

To 2 ml of the GLP-1 anti TfR-Fab fusion protein of Example 6 (containing about 92 nmol) was added 120 nmol VivoTag750-NHS, which is an amine reactive (NHS ester) near-infrared fluorochrome for labelling biomolecules for in vivo imaging applications, commercially available from PerkinElmer.

Usually this fluorescent label is fairly quantitatively attached to Fabs but in this case only very limited labelling was obtained. 600 nmol VivoTag750-NHS was added and the coupling proceeded overnight. Next day, the solution was applied to a PD-10 column (GE Healthcare) running in PBS and the labelled material collected in 1.6 ml PBS. The majority of the blue colour eluted later as hydrolysed tag. The concentration was determined to 32 nmol/ml by CLND (Chemiluminescent Nitrogen Detection) and the solution was aliquoted into 5 Eppendorf tubes with 320 µL in each and frozen.

LCMS showed a mixture 0, 1, 2, 3 labels per molecule (average about 1).

Example 9

Preparation of Fluorescence Labelled GLP-1 Control Fab Fusion Protein

Figure 9:
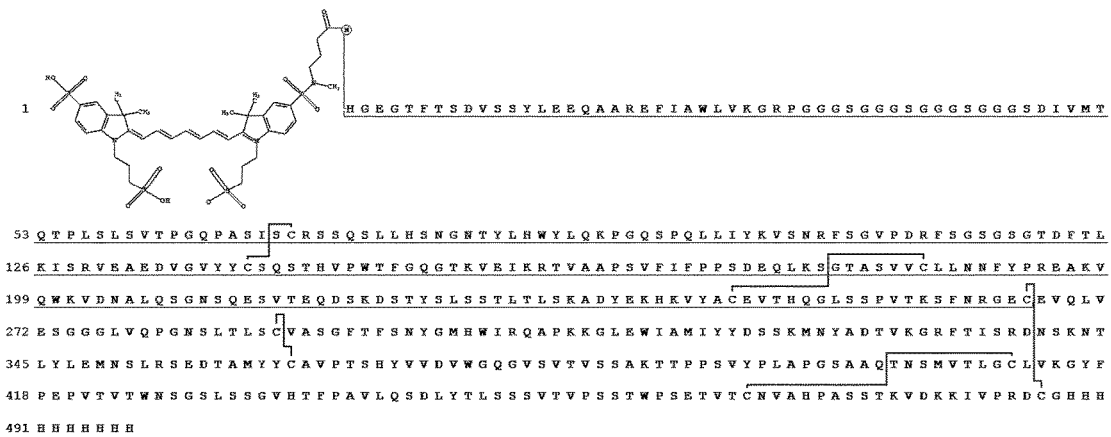
FIG. 9 shows the structure of a fluorescence labelled GLP-1 control Fab fusion protein (SEQ ID NO: 12), prepared as described in Example 9.

This example describes the fluorescence labelling of the GLP-1 control Fab fusion protein of Example 7 (SEQ ID NO: 12). The fluorescence labelled compound is shown in FIG. 9 (please note that the labelling is randomly attached and not just on the N-terminal as depicted).

To 2 ml of the GLP-1 control Fab fusion protein of Example 7 (SEQ ID NO: 12) (containing about 138 nmol) was added 160 nmol VivoTag750-NHS (PerkinElmer).

As described in Example 8 an additional amount of the fluorochrome had to be added, in this case 900 nmol. The coupling and collection of the labelled material was as described in Example 8 (in this case the labelled material was collected in 2 ml PBS). The majority of the blue colour eluted later as hydrolysed tag. The concentration was determined to 49 nmol/ml by CLND as described in Example 8, and the solution was aliquoted into 5 Eppendorf tubes with 400 µL in each and frozen.

LCMS showed a mixture of 0, 1, 2, 3 labels per molecule (average about 1).

Example 10

Synthesis of GLP-1 Peptide Used for Conjugation

Figure 10:
FIG. 10 shows the structure of a GLP-1 analogue (SEQ ID NO: 13), prepared as described in Example 10.

This example describes the synthesis of a GLP-1 peptide shown in FIG. 10.

The peptide of FIG. 10 without the bromo acetamide (BrAc) derivatisation at the epsilon amino group of the C-terminal Lys residue at position 58 has SEQ ID NO: 13 (position 58 corresponds to position 52 of SEQ ID NO: 13).

The peptide of SEQ ID NO: 13 may be defined as the analogue (8Aib, 22E, 26R, 34R) of GLP-1(7-37) with a C-terminal peptidic linker (viz., residues no. 38-58 added onto GLP-1(7-37), where residues 38-58 correspond to residues 32-52 of SEQ ID NO: 13). The peptide linker is: G-Q-A-P-G-Q-A-P-G-Q-A-P-G-Q-A-P-G-Q-A-P-K and has SEQ ID NO: 14.

The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH and Fmoc-Lys(Mtt)-OH, Fmoc-Aib-OH supplied from e.g. Anaspec, Bachem, Iris Biotech, or NovabioChem. Where nothing else is specified the natural L-form of the amino acids were used. The N-terminal amino acid was employed with N-terminal Boc protection at the alpha amino group (e.g. Boc-His(Trt)-OH). SPPS was performed using Fmoc based chemistry on a SymphonyX Solid Phase Peptide Synthesizer from Protein Technologies (Tucson, Ariz. 85714 U.S.A.). Preloaded Fmoc-Lys(Mtt)-wang LL resin (Novabiochem, loading 0.33 mmol/g) was used for the peptide synthesis. Fmoc-deprotection was achieved with 20% piperidine in DMF. Peptide double couplings for 1 h were performed in the first 20 cycles and single couplings for 2 h with capping (using acetic acid anhydride) in the rest. A mixture of Amino acid/Oxyma Pure/DIC solutions (0.3 M/0.3 M/0.3 M in DMF at a molar excess of 4 fold) were used for all couplings.

The resin was transferred to a glass reactor fitted with a filter. HFIP/DCM/TIPS 75:22:3 solution (70 ml) was added, stirred for 20 min, filtered and repeated 1× with additional 60 ml, and washed with DCM (3×65 ml) and DMF (3×65 ml).

A mixture of bromoacetic acid (3.0 g, 12 eq, 22 mmol) and DIC (1.39 g, 6 eq, 11 mmol) in DMF/DCM 1:1 (50 ml) was standing for 10 min and poured onto the resin. Standing 0/N, stirring. Filtered and washed with DMF (4×60 ml) and DCM (4×60 ml).

The peptide was cleaved from the resin by stirring in a mixture of (95 TFA:2.5 TIPS:2.5 water, 80 ml) for 3 h at RT. Filtered and the resin was washed with a small amount of TFA.

The solution was split into 12 plastic vials, and dry-ice cooled diethylether (25 ml) was added to each vial and filled up with an additional approximately 20 ml of ether. The precipitate was spinned down.

The supernatant was removed and the product was purified on preparative HPLC.

LCMS_34: Rt=2.37 min, M/4=1378.3

Example 11

Synthesis of GLP-1 Anti TfR-Fab Conjugate

This example describes the synthesis of a conjugate of a GLP-1 peptide and an anti TfR-Fab. The structure of the conjugate is shown in FIG. 11.

The element

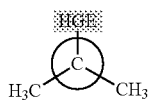

refers to the tripeptide of His-Aib-Glu (residues 434-436 of FIG. 11).

The N-terminal part of FIG. 11 (residues 1-433) is identical to the anti TfR-Fab of SEQ ID NO: 3 (see Examples 1 and 3).

The C-terminal part of FIG. 11 (residues 434-485) is identical to SEQ ID NO: 13 (see Example 10).

As shown in FIG. 11, the epsilon amino group of Lys 485 and the thiol group of Cys 377 are interconnected via Chem. 1: —CH$_2$—C(O)—.

To a solution of the anti TfR-Fab of Example 3 (41 ml with 252.4 mg, 5348 nmol of anti TfR-Fab) dissolved in PBS buffer, pH 7.4 was added 522 ul of a 200 mM EDTA buffer.

TCEP (5.05 μmol/ml, 1.05 eq., 1112 μL, 5615 nmol) was added to the protein solution.
Preparation of TCEP solution: TCEP, 0.5 M, pH 7, MW: 286 g/mol. 25 μL of the 0.5M TCEP solution was diluted with 2475 μL buffer (20 mM TEA, 2 mM EDTA, pH 8.5 buffer). Standing for about 2-3 h or until fully reduced.

The peptide from Example 10, 3.6 eq, was dissolved in DMSO (1.5 ml) and added to the Fab solution and the flask was rinsed with a little TRIS buffer pH 9. pH was adjusted with TRIS buffer pH 9 to pH 8.3 (start pH=6.5), standing 0/N.

The reaction mixture was concentrated by spinning in a Vivaspin 20, 10K filter to give 13 ml and was purified on an Äkta purifier from GE Healthcare.
Column: Hiload 26/600, superdex 200 pg SEC
Buffer: PBS-buffer, pH 7.4
The following characteristics of the resulting product were determined:
LCMS_36: Rt=3.52 min; m/30=1751.4; m/32=1642.0

Example 12

Synthesis of GLP-1 Control-Fab Conjugate

This example describes the synthesis of a conjugate of a GLP-1 peptide and a control Fab. The structure of the conjugate is shown in FIG. 12.

The element

Figure 12:
FIG. 12 shows the structure of a GLP-1 control Fab conjugate (SEQ ID NO: 5 and SEQ ID NO: 13), prepared as described in Example 12.

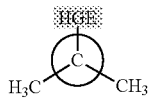

refers to the tripeptide of His-Aib-Glu (residues 439-441 of FIG. 12).

This conjugate was prepared by Cys alkylation of the control Fab of Example 4 with the bromo acetyl peptide of Example 10 (FIG. 10) using the same protocol as described in Example 11.

The N-terminal part of FIG. 12 (residues 1-438) is identical to the control Fab of SEQ ID NO: 5 (see Examples 2 and 4).

The C-terminal part of FIG. 12 (residues 439-490) is identical to SEQ ID NO: 13 (see Example 10).

As shown in FIG. 12, the epsilon amino group of Lys 490 and the thiol group of Cys 382 are interconnected via Chem. 1: —CH$_2$—C(O)—.

The following characteristics of the resulting product were determined:
LCMS_36: Rt=3.01 min; m/29=1832.1; m/31=1713.9

Example 13

Synthesis of GLP-1 Peptide Used for Conjugation

Figure 13:
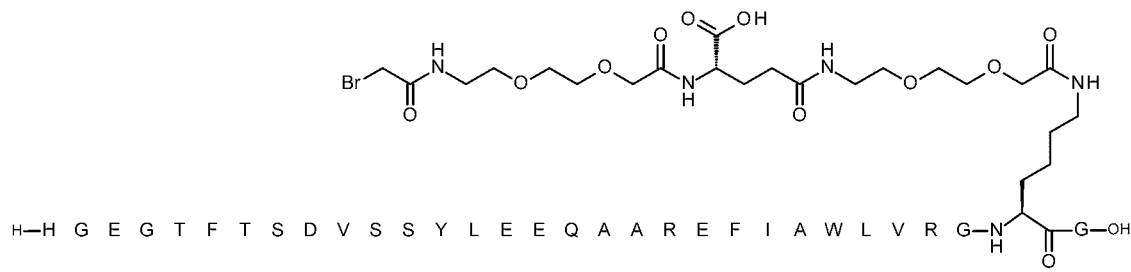
FIG. 13 shows the structure of a derivative of a GLP-1 analogue (SEQ ID NO: 15), prepared as described in Example 13.

This example describes the synthesis of a GLP-1 peptide derivative of FIG. 13.

FIG. 13 incorporates the GLP-1 analogue (8G, 22E, 26R, 34R, 36K) of GLP-1(7-37) (SEQ ID NO: 15).

FIG. 13 also incorporates a non-peptidic linker which can be defined as Chem. 5: -Ado-gGlu-Ado-, where Ado refers to 8-amino-3,6-dioxaoctanoic acid and gGlu to the amino acid Glu when attached to another molecule via an amide bond involving the carboxylic acid group at the gamma position of the side chain of Glu. A di-radical of Ado has the formula of Chem. 3: —NH—(CH$_2$)$_2$—O—(CH$_2$)$_2$—O—CH$_2$—C(O)—. A di-radical of gGlu has the formula of Chem. 4: —NH—CH(COOH)—(CH$_2$)$_2$—C(O)—). One Ado of the linker is attached to the epsilon amino group of the Lys residue at position 36 of the GLP-1 analogue. The other Ado of the linker is derivatised with bromoacetamide, for later conjugation to an anti-TfR Fab or a control Fab, as described in Examples 15 and 14, respectively.

The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH and Fmoc-Lys(Mtt)-OH, Fmoc-Aib-OH supplied from e.g. Anaspec, Bachem, Iris Biotech, or NovabioChem. Where nothing else is specified the natural L-form of the amino acids were used. The N-terminal amino acid was employed with N-terminal Boc protection at the alpha amino group (e.g. Boc-Tyr(tBu)-OH for peptides with Tyr at the N-terminus). SPPS was performed using Fmoc based chemistry on a SymphonyX Solid Phase Peptide Synthesizer from Protein Technologies (Tucson, Ariz. 85714 U.S.A.). Resins employed for the preparation of C-terminal peptide were Fmoc-Gly-wang LL resin (Novabiochem, loading e.g. 0.29 mmol/g). Fmoc-deprotection was achieved with 20% piperidine in DMF. Peptide couplings for 1 h were performed using Amino acid/Oxyma Pure/DIC solutions (0.3 M/0.3 M/0.3M in DMF at a molar excess of 4 fold). The Mtt group was removed by washing the resin with HFIP/TIS/DCM (75:2.5:22.5, v/v/v) (3×10 mL×30 min) before washing with DCM (5×10 mL). Synthesis was continued with Fmoc-Ado-OH and Fmoc-gGlu(OtBu)-OH as described above. The resin was transferred to a glass reactor fitted with a filter.

A mixture of bromoacetic acid (0.840 g, 12 eq, 6 mmol) and DIC (0.400 ml, 5.2 eq, 2.6 mmol) in DMF (16 ml) was standing for 10 min and poured onto the resin. Standing 0/N. Filtered and washed with DMF (4×6 ml) and DCM (4×6 ml).

The peptide was cleaved from the resin by stirring in a mixture of (95 TFA:2.5 TIPS:2.5 Water, 80 ml) for 3 h at RT. Filtered and the resin was washed with a small amount of TFA. The solution was split into 12 plastic vials and dry-ice cooled diethylether (25 ml) was added to each vial and filled up with an additional approximately 20 ml of ether. The precipitate was spinned down. The supernatant was removed and the product was purified on preparative HPLC.
LCMS_34: Rt=2.45 min, M/3=1328.2

Example 14

Synthesis of GLP-1 Control Fab Conjugate

This example describes the synthesis of a conjugate of a GLP-1 peptide and a control Fab. The structure of the conjugate is shown in FIG. 14.

This conjugate was prepared by Cys alkylation of the control Fab of Example 4 with the bromo acetyl peptide derivative of Example 13 (FIG. 13) using the same protocol as described in Example 11, except that the peptide derivative of Example 13 was used instead, in an amount of 3.6 eq.

Figure 14:
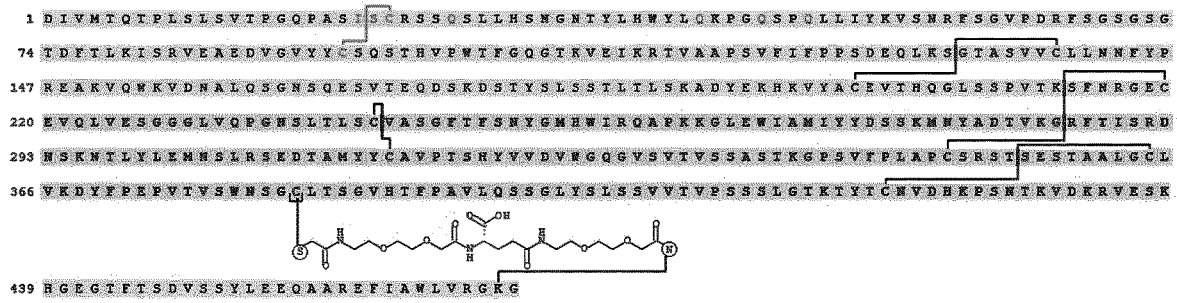
FIG. 14 shows the structure of a GLP-1 control Fab conjugate (SEQ ID NO: 5 and SEQ ID NO: 15 modified connecting the distal Ado of the linker of Chem. 5 (-Ado-gGlu-Ado-) to the thiol group of Cys 382 via Chem. 1 (—CH$_2$—C(O)—)) prepared as described in Example 14.

The N-terminal part of FIG. 14 (residues 1-438) is identical to the control Fab of SEQ ID NO: 5 (see Examples 2 and 4).

The C-terminal part of FIG. 14 (residues 439-469) is identical to FIG. 13, except for the fact that the distal Ado of the linker of Chem. 5: -Ado-gGlu-Ado- which is bromo acetamide derivatised in FIG. 13, is here connected to the thiol group of Cys 382 via a Chem. 1 chemical linker (Chem. 1: —$CH_2$—C(O)—). The entire linker thus is Chem. 2: —$CH_2$—C(O)-Ado-gGlu-Ado-.

The following characteristics of the resulting product were determined:
LCMS_36: Rt=3.14 min; m/30=1720.0; m/32=1612.6

Example 15: Synthesis of GLP-1 Anti TfR-Fab Conjugate

This example describes the synthesis of a conjugate of a GLP-1 peptide and an anti TfR-Fab. The structure of the conjugate is shown in FIG. 15.

This conjugate was prepared by Cys alkylation of the anti TfR-Fab of Example 3 with the bromo acetyl peptide derivative of Example 13 (FIG. 13) using the same protocol as described above for Example 14.

The N-terminal part of FIG. 15 (residues 1-433) is identical to the anti TfR-Fab of SEQ ID NO: 3 (see Examples 1 and 3).

The C-terminal part of FIG. 15 (residues 434-464) is identical to FIG. 13, except for the fact that the distal Ado of the linker of Chem. 5: -Ado-gGlu-Ado- which was bromo acetamide derivatised in FIG. 13 is here connected to the thiol group of Cys 377 via a chemical linker (Chem. 1: —$CH_2$—C(O)—). The entire linker thus is Chem. 2: —$CH_2$—C(O)-Ado-gGlu-Ado-.

The following characteristics of the resulting product were determined:
LCMS_36: Rt=3.55 min; m/30=1700.4; m/32=1594.2
Pharmacological Methods Example 16

In Vivo Imaging of Fluorescently Labelled GLP-1 TfR Fusion Proteins

This example examines the access to various GLP-1 receptor expressing areas of the brain of an "active" and an "inactive" GLP-1-Fab fusion protein ("active" in the sense that it binds to the TfR, "inactive" in the sense that it does not bind to the TfR). The two fusion proteins include one and the same GLP-1 receptor agonist compound but differ in the Fab part. This is for the purpose of determining if there is a substantial difference between the active and the inactive fusion protein in their access to brain areas that are protected by the blood brain barrier (BBB). The study is an acute study in mice.
Compound Administration:

Mice (C57BL/6J, male, Taconic, n=4/group) received a single i.v. dose of the fluorescence labelled GLP-1 anti TfR-Fab fusion protein of Example 8 ("GLP-1-Active TfR"), 120 nmol/kg, or of the fluorescence labelled GLP-1 control Fab fusion protein of Example 9 ("GLP-1-Inactive TfR"), 120 nmol/kg. The mice were anesthetised with isoflurane 6 hours ("6H") following administration of compound and euthanised by transcardiac perfusion with 10 ml heparinised (10 U/ml) saline followed by 10 ml 10% neutral buffered formalin (NBF). Brains were removed and immersed into 10% NBF and stored at 4° C. O/N until further processed.
Clearing of Tissue:

The brains were dehydrated and saturated in dibenzyl ether (DBE) to minimise scattering of light during scanning by removal of water, and by matching of the refractive index. Brain tissue was dehydrated at room temperature in graded tetrahydrofuran (THF) diluted in demineralised $H_2O$ (w/v) 50/80/96/99%/2×100% 6-12 hours for each step. The brains were then cleared at room temperature in 3×DBE for 6-12 hours each step.
Scanning with Light Sheet Fluorescence Microscopy (LSFM):

Brain samples were scanned using an UltraMicroscope II LSFM system (Lavision Biotec, Bielefeld, Germany) in 10.32 μm isotropic resolution. Data acquisition was performed using a 620/60 nm excitation filter and 680/30 nm emission filter for imaging autofluorescence, and a 710/75 nm excitation filter and 780/40 nm emission filter for imaging specific signals.
Image Analysis:

Images are single plane images of a z plane (2D). Spectral unmixing was performed to minimise the contribution of tissue auto-fluorescence in the images of the specific signals presented. The unmixing was carried out in Imaris (Release 7.6.5, Zurich, Switzerland) on imported tiff-files. The estimated auto-fluorescence contribution in the specific channel was calculated and removed based on ratios of voxel intensities between selected voxels in the unspecific recording and the corresponding voxels in the specific channel. A ratio was computed for 40 sets of voxels selected based on the histogram of the unspecific recording. The unmixing algorithm was written in Matlab (Release 2012b, Math Works, Natick, Massachusetts, United States) and applied as a XT-plugin in Imaris.

Images were registered to a common reference atlas space for visualisation and quantification using the Elastix software library version 4 (Klein, Stefan, et al. "Elastix: a toolbox for intensity-based medical image registration." IEEE transactions on medical imaging 29.1 (2010): 196-205). A source image $I_S(x)$ was registered to the target atlas image $I_T(x)$ by finding a coordinate transformation $T(x)$ that made $I_S(T(x))$ spatially aligned with $I_T(x)$. We used an affine coordinate transformation for initialisation followed by a nonrigid b-spline coordinate transformation which was iteratively optimised with respect to the mutual information between the source and the target. Registration parameters for mapping of LSFM data were similar to those used in Renier et al. Following image registration, a manual quality check was made for correct registration. If parts of the registered brains were out of alignment, the measurement connected to these individual regions were removed. Thus, for some brain regions, the number of samples varied between 3 and 4 within each group. Quantification was performed by summation of the unmixed intensity value of all voxels within the individual brain regions, indicating the total fluorescence signal from the compounds in these regions. The total signal is reported in arbitrary unit ("AU"). Total signal is a summation of the unmixed voxel intensity values in individual brain regions. The total signal thus indicates the total fluorescence signal from the compounds in these regions. (Renier, Nicolas, et al. "Mapping of Brain Activity by Automated Volume Analysis of Immediate Early Genes." Cell (2016)).

Results:

The results of the image analyses are shown in FIGS. 16A, 16B, 16C, and 16D.

In FIG. 16A, the total intensity of the fluorescently labelled compounds ("GLP-1-Active TfR" and "GLP-1-Inactive TfR") was quantified in brain regions expressing the GLP-1 receptor (GLP-1R). The total signal is reported in arbitrary unit (AU) and represents averages. FIG. 16B shows intensity of fluorescently labelled compounds in examples of circumventricular organs expressing the GLP-1R but devoid of a BBB. FIG. 16C shows intensity of fluorescently labelled compounds in examples of brain structures expressing the GLP-1R which are protected by the BBB. FIG. 16D shows intensity of fluorescently labelled compounds in examples of brain regions that do not express the GLP-1R. The abbreviations used for the various brain regions are defined in the list of abbreviations.

FIG. 16A shows that in the GLP-1R expressing regions the fluorescence signals were higher from the GLP-1-Active TfR compared to the GLP-1-Inactive TfR.

The differences between the active and inactive TfR compounds were smaller in the circumventricular organs expressing the GLP-1R but devoid of a BBB (FIG. 16B). The TfR is expressed both in capillaries and brain parenchyma. Thus, the slightly higher contribution from the active TfR compound in these regions indicates contribution from the TfR binding of the compounds in addition to binding by the GLP-1R.

The signals were also quantified in brain regions that do not express the GLP-1R (FIG. 16D). Here the signals were almost the same with both compounds where the slightly higher contribution from the active TfR compound again indicates contribution from the TfR binding of the compounds.

An example of brain structures which are protected by the BBB are given in FIG. 16C. Here the signal was highly increased from the GLP-1-Active TfR compared to the GLP-1-Inactive TfR indicating that the GLP-1 component was carried to regions not readily accessible for GLP-1 by itself. Although binding to the TfR may also contribute to this signal, the difference between the two compounds in regions expressing the GLP-1R is much larger than in regions without the GLP-1R (FIG. 16D). This suggests that the majority of the signal originated from binding to the GLP-1R.

Conclusion:

The distinct and marked difference in signal strength between the active and the inactive TfR compounds which is seen in the brain structures that are protected by the BBB (FIG. 16C) shows that the coupling of a GLP-1R agonist to an anti-TfR Fab can be used as a means to target GLP-1R agonists to areas of the brain which are not readily accessible by GLP-1R agonists. Some of these areas, such as the ACB, DMH, LHA, and LH have been shown to be important in regulation of body weight and reward related food intake.

Example 17: GLP-1 In Vitro Potency

The purpose of this example is to test the GLP-1 activity of the active and inactive GLP-1 fusions and conjugates disclosed herein (where the terms active/inactive refer to the ability to bind/not bind, respectively, to the transferrin receptor (TfR)). The GLP-1 activity is determined as GLP-1 in vitro potency and is the measure of human GLP-1 receptor activation in a whole cell assay.

Principle:

In vitro potency was determined by measuring the response of the human GLP-1 receptor in a reporter gene assay. The assay was performed in a stably-transfected BHK cell line that expresses the human GLP-1 receptor and contains the DNA for the cAMP response element (CRE) coupled to a promoter and the gene for firefly luciferase (CRE luciferase). When the human GLP-1 receptor is activated it results in the production of cAMP, which in turn results in the luciferase protein being expressed. When assay incubation is completed the luciferase substrate (luciferin) is added and the enzyme converts luciferin to oxyluciferin to produce bioluminescence. The luminescence is measured as the readout for the assay.

In order to test the binding of the compounds to albumin, the assay may be performed in the absence of serum albumin as well as in the presence of a considerably higher concentration of serum albumin (1.0% final assay concentration). An increase of the in vitro potency, $EC_{50}$ value, in the presence of serum albumin would indicate an affinity to serum albumin and represents a method to predict a protracted pharmacokinetic profile of the test substance in animal models.

Cell Culture and Preparation:

The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone. The cells were cultured at 5% $CO_2$ in Cell Culture Medium. They were aliquoted and stored in liquid nitrogen. Before each assay an aliquot was taken up and washed twice in PBS before being suspended at the desired concentration in the assay specific buffer. For 96-well plates the suspension was made to give a final concentration of $5 \times 10^3$ cells/well.

Materials:

The following chemicals were used in the assay: Pluronic F-68 (10% v/v) (Gibco 2404), human serum albumin (HSA) (Sigma A9511), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).

Buffers:

Cell Culture Medium consisted of DMEM medium with 10% w/v FBS (Fetal Bovine Serum; Invitrogen 16140-071), 1 mg/ml G418 (Invitrogen 15140-122), 240 nM MTX (methotrexate; Sigma M9929) and 1% w/v pen/strep (penicillin/streptomycin; Invitrogen 15140-122).

Assay Medium consisted of DMEM w/o phenol red, 10 mM Hepes and 1× Glutamax. The 1% Assay Buffer consisted of 2% ovalbumin, 0.2% Pluronic F-68 and 2% HSA in Assay Medium. The 0% Assay Buffer consisted of 2% w/v ovalbumin and 0.2% v/v Pluronic F-68 in Assay Medium.

Procedure:

1. Cell stocks were thawed in a 37° C. water bath.
2. Cells were washed three times in PBS.
3. The cells were counted and adjusted to $5\times10^3$ cells/50 µl ($1\times10^5$ cells/ml) in Assay Medium. A 50 µl aliquot of cells was transferred to each well in the assay plate.
4. Stocks of the test compounds were diluted to a concentration of 0.2 µM in 0% Assay Buffer for the 0% HSA CRE luciferase assay and 1% Assay Buffer for the 1% HSA CRE luciferase assay. Compounds were diluted 10-fold to give the following concentrations: $2\times10^{-7}$ M, $2\times10^{-8}$ M; $2\times10^{-9}$ M, $2\times10^{-10}$ M, $2\times10^{-11}$ M, $2\times10^{-12}$ M, $2\times10^{-13}$ M, and $2\times10^{-14}$ M.
5. A 50 µl aliquot of compound or blank was transferred from the dilution plate to the assay plate. Compounds were tested at the following final concentrations: $1\times10^{-7}$ M, $1\times10^{-8}$ M; $1\times10^{-9}$ M, $1\times10^{-10}$ M, $1\times10^{-11}$ M, $1\times10^{-12}$ M, $1\times10^{-13}$ M, and $1\times10^{-14}$ M.
6. The assay plate was incubated for 3 h in a 5% $CO_2$ incubator at 37° C.
7. The assay plate was removed from the incubator and allowed to stand at room temperature for 15 min.
8. A 100 µl aliquot of steadylite plus reagent was added to each well of the assay plate (reagent was light sensitive).
9. Each assay plate was covered with aluminum foil to protect it from light and shaken for 30 min at room temperature.
10. Each assay plate was read in a microtiter plate reader.

Calculations and Results:

The data from the plate reader were transferred to GraphPad Prism software. The software performed a non-linear regression (log(agonist) vs response). $EC_{50}$ values which were calculated by the software and reported in pM are shown in Table 1 below. A minimum of two replicates was measured for each sample on separate assay plates. The reported values are averages of the duplicates. For some examples more than one assay was run and in this case the data reported are the averages of the averaged duplicates.

TABLE 1

In vitro potency

| Compound of Example/Fig no. | Description | $EC_{50}$/pM (0% HSA) |
| --- | --- | --- |
| 5 | GLP-1 anti TNP-Fab fusion protein | 267 |
| 6 | GLP-1 anti TfR-Fab fusion protein | 48.3 |
| 7 | GLP-1 control Fab fusion protein | 52.4 |
| 8 | Vivotag 750 labelled GLP-1 anti TfR-Fab fusion protein | 92.8 |
| 9 | Vivotag 750 labelled GLP-1 control Fab fusion protein | 58.6 |
| 11 | GLP-1 anti TfR-Fab conjugate | 8.93 |
| 12 | GLP-1 control Fab conjugate | 3.00 |
| 14 | GLP-1 control Fab conjugate | 818 |
| 15 | GLP-1 anti TfR-Fab conjugate | 435 |

All compounds have potency data that confirms that they are GLP-1 receptor agonists. All compounds had a good GLP-1 in vitro potency corresponding to an $EC_{50}$ at 0% HSA of below 1000 pM.

Example 18: GLP-1 Receptor Binding

The purpose of this example is to test the GLP-1 receptor binding activity in vitro of the active and inactive GLP-1 fusions and conjugates disclosed herein (where the terms active/inactive refer to the ability to bind/not bind, respectively, to the transferrin receptor (TfR)). The receptor binding is a measure of the affinity of the compounds for the human GLP-1 receptor.

Principle:

The binding to the human GLP-1 receptor was measured in a competitive binding assay. In this type of assay a labelled ligand (in this case $^{125}$I-GLP-1) was bound to the receptor. Each test compound was added in a series of concentrations to isolated membranes containing the human GLP-1 receptor and displacement of the labelled ligand was monitored. The receptor binding was reported as the concentration at which half of the labelled ligand was displaced from the receptor, the $IC_{50}$ value. In order to test the binding of the derivatives to albumin, the assay may be performed in a very low concentration of serum albumin (max. 0.001% (w/v) final assay concentration as well as in the presence of a considerably higher concentration of serum albumin (2.0% (w/v) final assay concentration). An increase of the $IC_{50}$ value in the presence of serum albumin indicates an affinity to serum albumin.

Materials:

The following chemicals were used in the assay: human serum albumin (HSA) (Sigma A1653), DMEM w/o phenol red (Gibco 11880-028), Pen/strep (Invitrogen 15140-122), G418 (Invitrogen 10131-027), 1 M HEPES (Gibco 15630), EDTA (Invitrogen 15575-038), PBS (Invitrogen 14190-094), fetal calf serum (Invitrogen 16140-071), EGTA, $MgCl_2$ (Merck 1.05832.1000), Tween 20 (Amresco 0850C335), SPA particles (wheat germ agglutinin (WGA) SPA beads, Perkin Elmer RPNQ0001), $[^{125}I]$-GLP-1]-(7-36)$NH_2$ (produced in-house), OptiPlate™-96 (Packard 6005290).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM $MgCl_2$, 0.005% w/v Tween 20 and pH was adjusted to 7.4. An 8% albumin stock consisted of HSA dissolved at 8% (w/v) in assay buffer. An 0.02% albumin stock consisted of HSA dissolved at 0.02% (w/v) in assay buffer.

Cell Culture and Membrane Preparation:

The cells used in this assay (clone FCW467-12A) were BHK cells with BHKTS13 as a parent cell line. The cells express the human GLP-1 receptor. The cells were grown at 5% $CO_2$ in DMEM, 10% w/v fetal calf serum and 1% w/v Pen/Strep (Penicillin/Streptomycin). To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX™ dispersing instrument for 20-30 seconds in a suitable amount of buffer 1 (e.g., 10 ml). The homogenate was centrifuged for 15 minutes. The pellet was re-suspended (homogenised) in 10 ml buffer 2 and centrifuged. This step was repeated once more. The resulting pellet was re-suspended in buffer 2 and the protein concentration was determined. The membranes were aliquoted and stored at minus 80° C.

Procedure:

1. For the receptor binding assay in the presence of low HSA (0.001%) 50 µl of the assay buffer was added to each well of an assay plate. Assay continued with step 3.
2. For the receptor binding assay in the presence of high HSA (2.0%) 50 µl of the 8% albumin stock was added to each well of an assay plate. Assay continued with step 3.

3. Test compounds were serially diluted to give the following concentrations: $8\times10^{-7}$ M, $8\times10^{-8}$ M, $8\times10^{-9}$ M, $8\times10^{-10}$ M, $8\times10^{-11}$ M, $8\times10^{-12}$ M and $8\times10^{-13}$ M. Twenty-five µl were added to appropriate wells in the assay plate.
4. Cell membrane aliquots were thawed and diluted to their working concentration. Fifty µl were added to each well in the assay plate.
5. WGA SPA beads were suspended in assay buffer at 20 mg/ml. The suspension was diluted to 10 mg/ml in assay buffer just prior to addition to the assay plate. Fifty µl were added to each well in the assay plate.
6. The incubation was started by adding 25 µl of 480 pM solution of $[^{125}I]$-GLP-1]-(7-36)NH$_2$ to each well of the assay plate. A 25 µl aliquot was reserved for measuring total counts/well.
7. The assay plate was incubated for 2 h at 30° C.
8. The assay plate was centrifuged for 10 min.
9. The assay plate was read in a Packard TopCount NXT instrument.

Calculations:

The data from the TopCount instrument were transferred to GraphPad Prism software. The software averaged the values for the replicates and performed a non-linear regression. IC$_{50}$ values were calculated by the software and reported in nM.

Results:

The following results were obtained:

TABLE 2

GLP-1 receptor binding

| Compound of Example/Fig. no. | Description | IC$_{50}$/nM (low HSA) |
|---|---|---|
| 5 | GLP-1 anti TNP-Fab fusion protein | 12.5 |
| 6 | GLP-1 anti TfR-Fab fusion protein | 3.28 |
| 7 | GLP-1 control Fab fusion protein | 2.39 |
| 8 | Vivotag 750 labelled GLP-1 anti TfR-Fab fusion protein | 9.61 |
| 9 | Vivotag 750 labelled GLP-1 control Fab fusion protein | 3.89 |
| 11 | GLP-1 anti TfR-Fab conjugate | 0.99 |
| 12 | GLP-1 control Fab conjugate | 0.98 |
| 14 | GLP-1 control Fab conjugate | 55.9 |
| 15 | GLP-1 anti TfR-Fab conjugate | 32.5 |

All derivatives had an IC$_{50}$ (low albumin) below 60 nM.

Example 19: Transferrin Receptor Uptake Inhibition

The purpose of this example is to test the transferrin receptor binding activity in vitro of exemplary active and inactive GLP-1 fusions and conjugates disclosed herein (where the terms active/inactive refer to the ability to bind/not bind, respectively, to the transferrin receptor (TfR)). The transferrin receptor binding is a measure of affinity of a compound for the mouse transferrin receptor.

Principle:

The capacity of the conjugates of Examples 11-12 and 14-15 to inhibit the uptake of a transferrin receptor targeted antibody was measured in a competitive uptake assay. The two compounds in each set of Fab conjugates (Examples 11 and 12; and Examples 15 and 14) include the same GLP-1R agonist part but differ when it comes to the Fab part, which is "active" and "inactive", respectively, as regards binding to the TfR.

Each compound was added in a series of concentrations to a commercially available mouse fibroblast cell line (MEF-1) along with a set concentration of a fluorescently-labelled Fab fragment (described below). The inhibition of cellular uptake of the labelled Fab fragment by each compound was reported as the concentration at which half-maximal signal was obtained (IC$_{50}$ value).

Materials:

Preparation of Fluorescently-Labelled Fab Fragment:

The fluorescently-labelled Fab fragment was made by Cy5-labelling of the anti TfR-Fab of Example 1. The Cy5-labelled anti TfR-Fab is shown in FIG. 1B, where the Cy5 dye is shown attached to Cys at position 377.

226 uL of a 200 mM EDTA buffer was added to a solution of the anti TfR-Fab of Example 1 (6.15 mg/ml, 17.5 ml). 25 uL of a TCEP solution (0.5 M, pH 7.0) was diluted with 2475 ul buffer (20 mM TEA, 2 mM EDTA, pH 8.5). 517 uL (1.25 eq, 2.9 umol) of the diluted TCEP solution was added to to the anti TfR-Fab solution. The solution was stored at minus 80° C.

An aliquot of 1 mL (6.15 mg, 131 nmol) of the above produced solution was bobbled with argon, and 1 mg of Cy5 (Amersham Cy5 Maleimide Mono-Reactive Dye) dissolved in 100 uL dry DMF was added. The mixture was kept under argon night 0/N at 5° C.

The product was purified on a Zeba Spinn desalting column, 7K MWCO, 5 ml using the following protocol: Column spinned at 1000 G for 2 min. 2.4 ml washed out. Washed 3 timed with 2.4 ml PBS buffer, each time spinned at 1000 G for 2 min. After the 3. time the product (1 ml+0.7 ml wash) was placed on top of the column and spinned at 1000 G for 2 min. The product (1.7 ml) was collected. Calc. exact mass (m+z)/z (dimensionless): 47859.88. Found exact mass (m+z)/z (dimensionless): 47859.83.

The following additional chemicals were used in the assay:

DMEM (Gibco 31966-026), Pen/strep (Invitrogen 15140-122), G418 (Invitrogen 10131-027), 1 M HEPES (Gibco 15630), EDTA (Invitrogen 15575-038), fetal calf serum (Invitrogen 16140-071), PFA 4% (Chem Cruz Sc-281692), human serum albumin (Sigma A9511), collagen-coated imaging plate (Becton Dickinson 734-0319), DAPI Hoechst 33342 (Sigma B2261), Wheat germ agglutinin-Alexa 488 (Invitrogen W32464), HBSS (Gibco 14025).

Procedure:

1. Prior to seeding into the cell plates the MEF-1 cells were grown at 5% CO$_2$ in DMEM, 10% w/v fetal calf serum and 1% w/v penicillin/streptomycin. The day before each assay the cells were plated out at 5000 cells/well.
2. On the assay day the cells were washed with HBSS containing 0.1% (w/v) HSA.
3. Test compounds were serially diluted to give the following concentrations: $2\times10^{-6}$ M, $2\times10^7$ M, $2\times10^{-8}$ M, $2\times10^{-9}$ M, $2\times10^{-10}$ M, $2\times10^{-11}$ M, $2\times10^{-12}$ M and $2\times10^{-13}$ M. 100 µl of each was added to appropriate wells in the assay plate.
4. To each of the wells the fluorescently-labelled Fab fragment was added to a final concentration of 5 nM.
5. The plates were incubated at 37° C. for 15 min. After incubation the buffer was removed and the cells were washed with HBSS containing 0.1% (w/v) HSA.
6. Fifty µl of cold 4% PFA was added in a fume hood. The plates were incubated for 10 min at room temperature followed by removal of the PFA.
7. Fifty µl of a labelling solution was added to the plates and incubated for 10 min. The labelling solution contained DAPI at 1:200 (v/v; from 10 mg/ml stock) and WGA-Alexa488 at 1:200 (v/v; from 5 mg/ml stock). The assay plate was incubated for 10 min at room temperature.

8. The assay plate washed three times with 100 μl of HBSS and 100 μl of HBSS was added to each well after the wash steps.
9. The assay plate was read in a high-content imaging instrument (IN Cell 2200 instrument, GE).

Calculations:

The data from the IN Cell instrument was analysed using the software that was supplied with the instrument. Nuclei were defined using the DAPI-stained nuclei and cell boundaries were constructed based on the WGA-Alexa488 stainings. The amount of fluorescence that was internalised was calculated by defining granules visible in the Cy5 channel of the instrument and corresponded to internalised Cy5-labelled Fab fragment. The number and intensity of granules in each cell were calculated. The readout from the instrument that was used for further calculations was the total area of the granules divided by the number of cells in each acquisition field. A typical experiment contained 32 fields using a 20× microscope objective per well. The data were transferred to GraphPad Prism software and plotted as concentration response curves with log M (M is molarity of the test compounds) on the x-axis and total granule area per cell on the y-axis. The software performed a non-linear regression. $IC_{50}$ values were calculated by the software and reported in nM.

Results:

The following results were obtained:

TABLE 3

| Transferrin receptor uptake inhibition | | |
|---|---|---|
| Compound of Example/Fig. no. | Description | $IC_{50}$/nM |
| 11 | GLP-1 anti Tfr-Fab conjugate | 10.4 |
| 12 | GLP-1 control Fab conjugate | >1000 |
| 14 | GLP-1 control Fab conjugate | >1000 |
| 15 | GLP-1 anti TfR-Fab conjugate | 17.4 |

All derivatives with an active Fab (TfR-Fab) had an $IC_{50}$ value below 20 nM while all derivatives with an inactive Fab (control Fab) had an $IC_{50}$ of >1000 nM.

Example 20: In Vivo Studies in Mice

The purpose of this example is to assess whether GLP-1 anti TfR-Fab conjugates are biologically active in vivo, with focus on obesity related features.

Part I of the present example reports a study of the food intake lowering capability of an "active" GLP-1 anti TfR-Fab conjugate of the invention in lean mice, dosed acutely i.v.

Part II reports a comparison of this "active" conjugate with an "inactive" GLP-1 control-Fab conjugate, to determine whether the TfR arm contributes to the results obtained in Part I.

Part III reports a study in diet-induced obese mice, treated sub-chronically, with a view to investigating whether the reduced food intake observed in Parts I and II translates into a weight loss.

I. In Vivo Study of GLP-1 Anti TfR-Fab Conjugate of Example 11

Study Design:

Food intake was studied in lean, male C571316J mice (Taconic, Denmark) dosed acutely i.v. (0-100 nmol/kg) with the GLP-1 anti TfR-Fab conjugate of Example 11 over a 24 hour period using a biodaq automated monitoring system (Research Diets, New Brunswick, N.J., USA). Briefly, mice were maintained under a 12-hour light dark cycle with food (Altromin, Cat. no. 1314, Lippe, Germany) and tap water available ad lib. Prior to dosing, mice (n=4-6 per group) were assigned to 1 of 5 treatment groups that were evenly matched for body weight and placed in the biodaq system 8 days prior to dosing in order to acclimatise to testing and handling procedures. On the day of the experiment, mice were dosed i.v. at time 0 with either vehicle or the compound of Example 11 according to the table below:

TABLE 4

| Groups | | | | |
|---|---|---|---|---|
| Groups | | Dose nmol/kg | Conc. nmol/ml | Dose volume ml/kg | n |
| 1 | Vehicle* | — | — | 5 | 6 |
| 2 | Example 11 | 3 | 0.6 | 5 | 6 |
| 3 | Example 11 | 10 | 2 | 5 | 6 |
| 4 | Example 11 | 30 | 6 | 5 | 4 |
| 5 | Example 11 | 100 | 20 | 5 | 6 |

*PBS + 0.05% polysorbate 80

Plasma Exposure:

After 24 h, blood samples were taken via the sublingual plexus into EDTA tubes containing a protease inhibitor cocktail (3.097 g K3EDTA (MW 406.53), Fluka 03665, dissolved in 50 ml Trasylol, 10.000 KIU (kallikrein inactivator units), 0.5 ml 20 mM Val-Pyr (16.48 mg Val-pyr/4 ml $H_2O$ pH is regulated to 7.4 by 1 M HCl) intended to stabilise the peptide during plasma analysis. Afterwards, animals were euthanised by exsanguination followed by cervical dislocation while under anaesthesia. Blood samples were kept on ice and centrifuged (4 min×4000 g) within 30 min, at 4° C. 50 μl plasma was then aliquoted into appropriately labelled tubes, placed on dry ice, and stored at minus 80° C., until analysis.

Plasma concentrations of the compound of Example 11 (and for Parts II and III also the compound of Example 12) were measured by LOCI (Luminescent Oxygen Channelling Immunoassay). In brief, the LOCI reagents included two latex bead reagents (donor and acceptor beads) and a biotinylated monoclonal antibody recognising an N-terminus epitope of GLP-1. The donor bead reagent, containing a photosensitive dye, was coated with streptavidin. The second bead reagent, the acceptor beads, was conjugated with another monoclonal antibody specific for the C-terminus of GLP-1, which made up the sandwich. During the assay, the three reactants were combined with the compound of Example 11 (or, in part II and III, either the compound of Example 11 or the compound of Example 12) in the plasma to form a bead-aggregate immuno-complex. Excitations of the complex released singlet oxygen molecules from the donor beads, which were channelled into the acceptor beads and triggered a chemiluminescence response that was measured in the EnVision plate reader. The amount of light generated, reported as counts per second (cps), was proportional to the concentration of the analyte.

All calibrators, QC-samples and unknown samples in EDTA plasma were analysed in quadruplicates determinations.

The analytical procedure was as follows:
Working solutions of both acceptor beads/biotinylated antibody and donor beads were prepared in LOCI buffer.
One μL plasma sample/calibrator/QC was applied per well.

15 µL of the working solution containing biotinylated monoclonal antibody recognising an N-terminus epitope of GLP-1 and acceptor beads coated with monoclonal antibody specific for the C-terminus of GLP-1 were added to each well.

The plates were sealed and covered with a black lid.

The assay was allowed to incubate for 1 hour at 18-22° C.

30 µL of streptavidin-coated donor beads diluted in LOCI buffer was added under the green light.

The plate was covered with a black lid and incubated for 30 minutes at 18-22° C. Finally, the plate was read in Envision.

The analysis was carried out using an Envision reader controlled by Envision software. The instrument response (counts per seconds) was exported to LOCI Calculator, where plasma concentrations were calculated.

Calibrators: A dilution line of the compound of Example 11 calibrator (and for parts II and III also of the compound of Example 12 calibrator) was prepared in a mouse plasma pool covering a range from 400.000 to 42 pmol/L. The mouse plasma pool was included as the 0 pM calibrator (blank). The calibrators were stored in Micronic tube at minus 18° C.

Performance:

Lower limit of quantification (LoQ) was determined to be 40 pmol/L. Upper limit of quantification (ULoQ) was determined to 25.000 pM. The imprecision (CV) was assessed by the measurement of three samples in 12 consecutive analytical runs and 21 determinations of each of the three samples in the same analytical run; the overall CV was <10%.

Materials:
Reagents:

LOCI buffer: 25 mM Hepes (Sigma H-3375), 50 mM NaCl (Merck 8.22184), 10 mM K-EDTA (Fluka 03664), 2 mg/ml Dextran (Pharmacosmos 551005009007), 0.5% ovalbumin OA (Sigma-A 5573), 0.05% BGG (Sigma G-7516), 0.1% Tween20 (Merck 8.22184), 0.01% Proclin 300 (Sigma-Aldrich 48912-U), 0.01% Gentamycin (Biol. Indust. 03-035-1), 0.2 mg/ml HBR1 (Scan. Lab. 3KC533), pH 7.4

Mouse Plasma for Dilutions and Calibrators:

Female mouse plasma (C57BL/6) from Bioreclamation, K2 EDTA, Cat. MSEPLEDTA2-057-F Assay Plates:

Perkin Elmer, PPN 6005359.

Data Analysis:

Graph Pad® software was used for all analyses; data is presented as mean. Statistical analysis was performed using 2-way ANOVA followed by Bonferroni's multiple comparisons test comparing all groups.

Results:

The results are shown in FIG. 17, where FIG. 17A shows cumulative food intake (FI) in g, and FIG. 17B plasma exposure levels in pM measured 24 h after dosing. Data is shown as mean values.

From FIG. 17A it is clear that the compound of Example 11 lowered food intake in a dose-dependent manner. And FIG. 17B shows that the higher the dose the higher the plasma exposure. This confirms that the compound is biologically active in vivo.

II. Head-to-Head In Vivo Study of "Active" and "Inactive" Compounds of Examples 11 and 12

To determine whether the TfR arm in the GLP-1 anti TfR-Fab conjugate of Example 11 contributed to the food intake lowering ability as determined above, a head-to-head comparison was performed with the GLP-1 control-Fab conjugate of Example 12, in which the same GLP-1R agonist is conjugated to an inactive Fab, to serve as a control compound.

Briefly, lean C571316J mice were maintained under a 12-h light dark cycle (lights off 11 a.m.), with food and water available ad lib, as in part I above. Also similarly to part I above, mice were habituated to the biodaq food intake monitoring system for 7 days prior to being assigned into 1 of 3 treatment groups that were evenly matched for body weight. On the day of the experiment, mice were dosed with either vehicle or 100 nmol/kg of the compound of Example 11 or the compound of Example 12 according to the table below:

TABLE 5

| Groups | | | | |
|---|---|---|---|---|
| Groups | Dose nmol/kg | Conc. nmol/ml | Dose volume ml/kg | n = |
| 1 Vehicle* | — | — | 5 | 10 |
| 2 Example 11 | 100 | 20 | 5 | 11 |
| 3 Example 12 | 100 | 20 | 5 | 11 |

*PBS + 0.05% polysorbate 80

Food intake was monitored hourly over the next 24 h, after which mice were sacrificed by exsanguination followed by cervical dislocation while under anaesthesia.

A satellite group of mice were used to generate exposure profiles of each compound. Blood samples were taken via the sublingual plexus into EDTA tubes containing a protease inhibitor cocktail and plasma was collected and analysed for exposure, as described in part I above. For each compound, blood draws were taken via sparse sampling, n=3 mice per time point, after 1 h, 4 h, 8 h, 10 h, 16 h, 18 h, and 24 h after i.v. dosing. Plasma samples were analysed for exposure as described in part I above.

Data Analysis:

Graph Pad® software was used for all analyses; data is presented as mean. Statistical analysis was performed using 2-way ANOVA followed by Bonferroni's multiple comparisons test comparing all groups.

Results:

The results are shown in FIG. 18, where FIG. 18A shows cumulative food intake (FI) in g, and FIG. 18B shows plasma exposure levels (plasma concentration in pM) measured over 24 h.

From FIG. 18A it is clear that both GLP-1 compounds reduced food intake relative to vehicle treated mice over 24 h of observation. However, food intake lowering was significantly greater in mice treated with the compound of Example 11 relative to mice treated with the compound of Example 12. FIG. 18B shows that plasma exposure levels were similar or greater in mice treated with the control compound of Example 12 implying that differences in food intake lowering among analogues were unrelated to differences in PK. Rather, these data demonstrate that the active TfR Fab in the compound of Example 11 contributed to greater food intake lowering.

III. Sub-Chronical In Vivo Study in Diet-Induced Obese Mice with "Active" and "Inactive" Compounds of Examples 11 and 12, Determination of Weight Loss To determine whether reductions in acute food intake lowering translated to weight loss in a preclinical model of obesity, we next compared the compounds used in Parts I and II above in DIO mice treated sub-chronically for 19 days. Briefly, Male C571316J mice (Charles River, France) (n=79) were maintained on a 60% high fat diet (D12492, Research Diets, New Brunswick, N.J., USA) beginning at approximately 4 weeks of age. Obese mice were shipped to the test facility at approximately 20 weeks of age, and were housed in a temperature and humidity controlled environment, n=10 per cage, under a 12-12 h light-dark cycle (Lights off 11:00 p.m.). After 4 days, mice in the high-fat diet fed group were switched from 60% to 45% high-fat diet (HFD D12451, Research Diets, New Brunswick, N.J., USA) to prevent crumbling and spillage and more accurately measure food intake. All mice were singly housed at this time and allowed to acclimatise to their new environment for two additional weeks. Food and water were available ad lib at all times.

Body composition (Echo MRI 700, Houston, Tex., USA) was measured on day 5 prior to dosing, and on day 3 prior to dosing mice were assigned into 1 of 3 treatment groups evenly matched for fat and lean tissue mass.

Food intake and body weight were monitored daily, beginning the day before dosing. Compounds were administered daily each day beginning at 12:30 p.m. starting on day 1 and according to Table 6 below. Mice were initially dosed i.v. on days 1-4 and then s.c. on days 5-19. Blood samples for plasma exposure were collected 2 h after dosing on day 19 and analysed as described in Part I above.

TABLE 6

| Group | Treatment | ml/kg | n = | i.v. dosing days 1-4 | s.c. dosing days 5-19 |
|---|---|---|---|---|---|
| 1 | Vehicle* | 5 | 11 | — | — |
| 2 | Example 11 | 5 | 11 | 100 nmol/kg/day | 100 nmol/kg/day |
| 3 | Example 12 | 5 | 11 | 100 nmol/kg/day | 100 nmol/kg/day |

*PBS + 0.05% polysorbate 80

Results:

The results are shown in FIG. 19, where FIG. 19A shows mean weight loss (%), and FIG. 19B shows mean plasma concentration (pM) measured 2 h after dosing on day 19.

From FIG. 19A it is clear that both compounds lowered body weight compared to vehicle treated mice. FIG. 19B shows differences in plasma exposure levels were similar among groups, however, DIO mice treated with the "active" compound of Example 11 lost more weight than DIO mice treated with the "inactive" compound of Example 12, showing that the "active" compound with the TfR Fab conferred an additional benefit to body weight lowering compared to the control compound.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A construct comprising a GLP-1 analogue and means for binding allosterically to the transferrin receptor (TfR); or a pharmaceutically acceptable salt, amide, or ester thereof.

2. The construct according to claim 1, wherein the GLP-1 analogue is semaglutide.

3. The construct according to claim 1, wherein the GLP-1 analogue comprising the amino acid sequence of SEQ ID NO: 13.

4. The construct according to claim 1, further comprising a linker between the GLP-1 analogue and the means for binding allosterically to the TfR.

5. A construct comprising semaglutide, a linker, and means for binding allosterically to the transferrin receptor (TfR); or a pharmaceutically acceptable salt, amide, or ester thereof.

6. A construct comprising a GLP-1 analogue, a linker, and means for binding allosterically to the transferrin receptor (TfR); or a pharmaceutically acceptable salt, amide, or ester thereof; wherein the GLP-1 analogue comprising the amino acid sequence of SEQ ID NO: 13.

* * * * *

SEQUENCE LISTING

<160> NUMBER OF SEQ ID NOS: 18

<210> SEQ ID NO 1
<211> LENGTH: 214
<212> TYPE: PRT
<213> ORGANISM: Artificial Sequence
<220> FEATURE:
<223> OTHER INFORMATION: Light chain of anti TfR-Fab

<400> SEQUENCE: 1

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
                20                  25                  30

Leu Ala Trp Tyr Gln Gln Lys Pro Gly Lys Ser Pro Gln Leu Leu Ile
            35                  40                  45

Tyr Gly Ala Thr Ser Leu Ala Asp Gly Val Pro Ser Arg Phe Ser Gly
        50                  55                  60

Ser Arg Ser Gly Thr Gln Phe Ser Leu Lys Ile Ser Arg Val Gln Val
65                  70                  75                  80

Glu Asp Ile Gly Ile Tyr Tyr Cys Leu Gln Ala Tyr Asn Thr Pro Trp
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 219
<212> TYPE: PRT
<213> ORGANISM: Artificial Sequence
<220> FEATURE:
<223> OTHER INFORMATION: Heavy chain of anti TfR-Fab

<400> SEQUENCE: 2

Glu Val Gln Leu Val Glu Ser Gly Gly Gly Leu Val Gln Pro Gly Asn
1               5                   10                  15

Ser Leu Thr Leu Ser Cys Val Ala Ser Gly Phe Thr Phe Ser Asn Tyr
            20                  25                  30

Gly Met His Trp Ile Arg Gln Ala Pro Lys Lys Gly Leu Glu Trp Ile
        35                  40                  45

Ala Met Ile Tyr Tyr Asp Ser Ser Lys Met Asn Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Val Pro Thr Ser His Tyr Val Val Asp Val Trp Gly Gln Gly Val
            100                 105                 110

Ser Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Cys Leu Thr Ser Gly Val His Thr Phe Pro Ala Val Leu Gln
                165                 170                 175

Ser Ser Gly Leu Tyr Ser Leu Ser Val Val Thr Val Pro Ser Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys
    210                 215

<210> SEQ ID NO 3
<211> LENGTH: 433
<212> TYPE: PRT
<213> ORGANISM: Artificial Sequence
<220> FEATURE:
<223> OTHER INFORMATION: Anti TfR-Fab
<220> FEATURE:
```

-continued

```
<221> NAME/KEY: DISULFID
<222> LOCATION: (23)..(88)
<220> FEATURE:
<221> NAME/KEY: DISULFID
<222> LOCATION: (134)..(194)
<220> FEATURE:
<221> NAME/KEY: DISULFID
<222> LOCATION: (214)..(346)
<220> FEATURE:
<221> NAME/KEY: DISULFID
<222> LOCATION: (236)..(310)
<220> FEATURE:
<221> NAME/KEY: DISULFID
<222> LOCATION: (359)..(415)

<400> SEQUENCE: 3

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60

Ser Arg Ser Gly Thr Gln Phe Ser Leu Lys Ile Ser Arg Val Gln Val
65                  70                  75                  80

Glu Asp Ile Gly Ile Tyr Tyr Cys Leu Gln Ala Tyr Asn Thr Pro Trp
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Val Gln Leu Val Glu Ser Gly Gly Gly
    210                 215                 220

Leu Val Gln Pro Gly Asn Ser Leu Thr Leu Ser Cys Val Ala Ser Gly
225                 230                 235                 240

Phe Thr Phe Ser Asn Tyr Gly Met His Trp Ile Arg Gln Ala Pro Lys
                245                 250                 255

Lys Gly Leu Glu Trp Ile Ala Met Ile Tyr Tyr Asp Ser Ser Lys Met
            260                 265                 270

Asn Tyr Ala Asp Thr Val Lys Gly Arg Phe Thr Ile Ser Arg Asp Asn
        275                 280                 285

Ser Lys Asn Thr Leu Tyr Leu Glu Met Asn Ser Leu Arg Ser Glu Asp
    290                 295                 300

Thr Ala Met Tyr Tyr Cys Ala Val Pro Thr Ser His Tyr Val Val Asp
305                 310                 315                 320

Val Trp Gly Gln Gly Val Ser Val Thr Val Ser Ser Ala Ser Thr Lys
                325                 330                 335
```

Gly Pro Ser Val Phe Pro Leu Ala Pro Cys Ser Arg Ser Thr Ser Glu
            340                 345                 350

Ser Thr Ala Ala Leu Gly Cys Leu Val Lys Asp Tyr Phe Pro Glu Pro
        355                 360                 365

Val Thr Val Ser Trp Asn Ser Gly Cys Leu Thr Ser Gly Val His Thr
    370                 375                 380

Phe Pro Ala Val Leu Gln Ser Ser Gly Leu Tyr Ser Leu Ser Ser Val
385                 390                 395                 400

Val Thr Val Pro Ser Ser Ser Leu Gly Thr Lys Thr Tyr Thr Cys Asn
                405                 410                 415

Val Asp His Lys Pro Ser Asn Thr Lys Val Asp Lys Arg Val Glu Ser
            420                 425                 430

Lys

<210> SEQ ID NO 4
<211> LENGTH: 219
<212> TYPE: PRT
<213> ORGANISM: Artificial Sequence
<220> FEATURE:
<223> OTHER INFORMATION: Light chain of control Fab

<400> SEQUENCE: 4

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 438
<212> TYPE: PRT
<213> ORGANISM: Artificial Sequence
<220> FEATURE:

```
<223> OTHER INFORMATION: Control Fab
<220> FEATURE:
<221> NAME/KEY: DISULFID
<222> LOCATION: (23)..(93)
<220> FEATURE:
<221> NAME/KEY: DISULFID
<222> LOCATION: (139)..(199)
<220> FEATURE:
<221> NAME/KEY: DISULFID
<222> LOCATION: (219)..(351)
<220> FEATURE:
<221> NAME/KEY: DISULFID
<222> LOCATION: (241)..(315)
<220> FEATURE:
<221> NAME/KEY: DISULFID
<222> LOCATION: (364)..(420)

<400> SEQUENCE: 5
```

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Glu Val Gln Leu Val
    210                 215                 220

Glu Ser Gly Gly Gly Leu Val Gln Pro Gly Asn Ser Leu Thr Leu Ser
225                 230                 235                 240

Cys Val Ala Ser Gly Phe Thr Phe Ser Asn Tyr Gly Met His Trp Ile
                245                 250                 255

Arg Gln Ala Pro Lys Lys Gly Leu Glu Trp Ile Ala Met Ile Tyr Tyr
            260                 265                 270

Asp Ser Ser Lys Met Asn Tyr Ala Asp Thr Val Lys Gly Arg Phe Thr
        275                 280                 285

Ile Ser Arg Asp Asn Ser Lys Asn Thr Leu Tyr Leu Glu Met Asn Ser
    290                 295                 300

Leu Arg Ser Glu Asp Thr Ala Met Tyr Tyr Cys Ala Val Pro Thr Ser
305                 310                 315                 320

His Tyr Val Val Asp Val Trp Gly Gln Gly Val Ser Val Thr Val Ser
            325                 330                 335

Ser Ala Ser Thr Lys Gly Pro Ser Val Phe Pro Leu Ala Pro Cys Ser
            340                 345                 350

Arg Ser Thr Ser Glu Ser Thr Ala Ala Leu Gly Cys Leu Val Lys Asp
            355                 360                 365

Tyr Phe Pro Glu Pro Val Thr Val Ser Trp Asn Ser Gly Cys Leu Thr
            370                 375                 380

Ser Gly Val His Thr Phe Pro Ala Val Leu Gln Ser Ser Gly Leu Tyr
385                 390                 395                 400

Ser Leu Ser Ser Val Val Thr Val Pro Ser Ser Ser Leu Gly Thr Lys
            405                 410                 415

Thr Tyr Thr Cys Asn Val Asp His Lys Pro Ser Asn Thr Lys Val Asp
            420                 425                 430

Lys Arg Val Glu Ser Lys
            435

<210> SEQ ID NO 6
<211> LENGTH: 266
<212> TYPE: PRT
<213> ORGANISM: Artificial Sequence
<220> FEATURE:
<223> OTHER INFORMATION: Light chain of GLP-1 anti TNP-Fab fusion
      protein

<400> SEQUENCE: 6

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Lys Gly Arg Pro Gly
            20                  25                  30

Gly Gly Ser Gly Gly Gly Ser Gly Gly Ser Gly Gly Gly Ser Asp
            35                  40                  45

Ile Val Met Thr Gln Thr Pro Leu Ser Leu Ser Val Thr Pro Gly Gln
50                  55                  60

Pro Ala Ser Ile Ser Cys Arg Ser Ser Gln Ser Leu Leu His Ser Asn
65                  70                  75                  80

Gly Asn Thr Tyr Leu His Trp Tyr Leu Gln Lys Pro Gly Gln Ser Pro
            85                  90                  95

Gln Leu Leu Ile Tyr Lys Val Ser Asn Arg Phe Ser Gly Val Pro Asp
            100                 105                 110

Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ser Gln Ser Thr
            130                 135                 140

His Val Pro Trp Thr Phe Gly Gln Gly Thr Lys Val Glu Ile Lys Arg
145                 150                 155                 160

Thr Val Ala Ala Pro Ser Val Phe Ile Phe Pro Pro Ser Asp Glu Gln
            165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
            195                 200                 205

Gly Asn Ser Gln Glu Ser Val Thr Glu Gln Asp Ser Lys Asp Ser Thr
            210                 215                 220

Tyr Ser Leu Ser Ser Thr Leu Thr Leu Ser Lys Ala Asp Tyr Glu Lys
225                 230                 235                 240

```
His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 7
<211> LENGTH: 227
<212> TYPE: PRT
<213> ORGANISM: Artificial Sequence
<220> FEATURE:
<223> OTHER INFORMATION: Heavy chain of GLP-1 anti TNP-Fab fusion
      protein
<220> FEATURE:
<221> NAME/KEY: MOD_RES
<222> LOCATION: (1)..(1)
<223> OTHER INFORMATION: Q is pyroglutamic acid

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Tyr Trp Asn Trp Ile Arg Gln Pro Pro Gly Lys Gly Leu Glu Trp Ile
        35                  40                  45

Gly Thr Ile Ser Tyr Ser Gly Asp Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Gly Ser Tyr Val Phe Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys His His His His His His
    210                 215                 220

His His His
225

<210> SEQ ID NO 8
<211> LENGTH: 493
<212> TYPE: PRT
<213> ORGANISM: Artificial Sequence
<220> FEATURE:
<223> OTHER INFORMATION: GLP-1 anti TNP-Fab fusion protein
<220> FEATURE:
<221> NAME/KEY: DISULFID
<222> LOCATION: (70)..(140)
<220> FEATURE:
<221> NAME/KEY: DISULFID
```

```
<222> LOCATION: (186)..(246)
<220> FEATURE:
<221> NAME/KEY: DISULFID
<222> LOCATION: (266)..(396)
<220> FEATURE:
<221> NAME/KEY: DISULFID
<222> LOCATION: (288)..(361)
<220> FEATURE:
<221> NAME/KEY: DISULFID
<222> LOCATION: (409)..(465)

<400> SEQUENCE: 8

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Lys Gly Arg Pro Gly
                20                  25                  30

Gly Gly Ser Gly Gly Gly Ser Gly Gly Gly Ser Gly Gly Gly Ser Asp
            35                  40                  45

Ile Val Met Thr Gln Thr Pro Leu Ser Leu Ser Val Thr Pro Gly Gln
50                  55                  60

Pro Ala Ser Ile Ser Cys Arg Ser Ser Gln Ser Leu Leu His Ser Asn
65                  70                  75                  80

Gly Asn Thr Tyr Leu His Trp Tyr Leu Gln Lys Pro Gly Gln Ser Pro
                85                  90                  95

Gln Leu Leu Ile Tyr Lys Val Ser Asn Arg Phe Ser Gly Val Pro Asp
                100                 105                 110

Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ser Gln Ser Thr
130                 135                 140

His Val Pro Trp Thr Phe Gly Gln Gly Thr Lys Val Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys Gln Val Gln Leu Gln Glu
            260                 265                 270

Ser Gly Pro Gly Leu Val Lys Pro Ser Glu Thr Leu Ser Leu Thr Cys
        275                 280                 285

Thr Val Ser Gly Gly Ser Ile Ser Ser Gly Tyr Trp Asn Trp Ile Arg
290                 295                 300

Gln Pro Pro Gly Lys Gly Leu Glu Trp Ile Gly Thr Ile Ser Tyr Ser
305                 310                 315                 320

Gly Asp Thr Tyr Tyr Asn Pro Ser Leu Lys Ser Arg Val Thr Ile Ser
                325                 330                 335

Val Asp Thr Ser Lys Asn Gln Phe Ser Leu Lys Leu Ser Ser Val Thr
            340                 345                 350
```

```
Ala Ala Asp Thr Ala Val Tyr Tyr Cys Ala Arg Tyr Gly Ser Tyr Val
            355                 360                 365

Phe Asp Tyr Trp Gly Gln Gly Thr Thr Val Thr Val Ser Ser Ala Ser
370                 375                 380

Thr Lys Gly Pro Ser Val Phe Pro Leu Ala Pro Cys Ser Arg Ser Thr
385                 390                 395                 400

Ser Glu Ser Thr Ala Ala Leu Gly Cys Leu Val Lys Asp Tyr Phe Pro
                405                 410                 415

Glu Pro Val Thr Val Ser Trp Asn Ser Gly Ala Leu Thr Ser Gly Val
            420                 425                 430

His Thr Phe Pro Ala Val Leu Gln Ser Ser Gly Leu Tyr Ser Leu Ser
            435                 440                 445

Ser Val Val Thr Val Pro Ser Ser Ser Leu Gly Thr Lys Thr Tyr Thr
450                 455                 460

Cys Asn Val Asp His Lys Pro Ser Asn Thr Lys Val Asp Lys Arg Val
465                 470                 475                 480

Glu Ser Lys His His His His His His His His
                485                 490

<210> SEQ ID NO 9
<211> LENGTH: 261
<212> TYPE: PRT
<213> ORGANISM: Artificial Sequence
<220> FEATURE:
<223> OTHER INFORMATION: Light chain of GLP-1 anti TfR-Fab fusion
      protein

<400> SEQUENCE: 9

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Lys Gly Arg Pro Gly
            20                  25                  30

Gly Gly Ser Gly Gly Gly Ser Gly Gly Gly Ser Gly Gly Gly Ser Asp
        35                  40                  45

Ile Gln Met Thr Gln Ser Pro Ala Ser Leu Ser Ala Ser Leu Glu Glu
50                  55                  60

Ile Val Thr Ile Thr Cys Gln Ala Ser Gln Asp Ile Gly Asn Trp Leu
65                  70                  75                  80

Ala Trp Tyr Gln Gln Lys Pro Gly Lys Ser Pro Gln Leu Leu Ile Tyr
            85                  90                  95

Gly Ala Thr Ser Leu Ala Asp Gly Val Pro Ser Arg Phe Ser Gly Ser
        100                 105                 110

Arg Ser Gly Thr Gln Phe Ser Leu Lys Ile Ser Arg Val Gln Val Glu
    115                 120                 125

Asp Ile Gly Ile Tyr Tyr Cys Leu Gln Ala Tyr Asn Thr Pro Trp Thr
130                 135                 140

Phe Gly Gly Gly Thr Lys Leu Glu Leu Lys Arg Ala Asp Ala Ala Pro
145                 150                 155                 160

Thr Val Ser Ile Phe Pro Pro Ser Ser Glu Gln Leu Thr Ser Gly Gly
            165                 170                 175

Ala Ser Val Val Cys Phe Leu Asn Asn Phe Tyr Pro Lys Asp Ile Asn
        180                 185                 190

Val Lys Trp Lys Ile Asp Gly Ser Glu Arg Gln Asn Gly Val Leu Asn
    195                 200                 205

Ser Trp Thr Asp Gln Asp Ser Lys Asp Ser Thr Tyr Ser Met Ser Ser
210                 215                 220
```

```
Thr Leu Thr Leu Thr Lys Asp Glu Tyr Glu Arg His Asn Ser Tyr Thr
225                 230                 235                 240

Cys Glu Ala Thr His Lys Thr Ser Thr Ser Pro Ile Val Lys Ser Phe
            245                 250                 255

Asn Arg Asn Glu Cys
            260
```

```
<210> SEQ ID NO 10
<211> LENGTH: 231
<212> TYPE: PRT
<213> ORGANISM: Artificial Sequence
<220> FEATURE:
<223> OTHER INFORMATION: Heavy chain of GLP-1 anti TfR-Fab fusion
      protein

<400> SEQUENCE: 10
```

```
Glu Val Gln Leu Val Glu Ser Gly Gly Gly Leu Val Gln Pro Gly Asn
1               5                   10                  15

Ser Leu Thr Leu Ser Cys Val Ala Ser Gly Phe Thr Phe Ser Asn Tyr
            20                  25                  30

Gly Met His Trp Ile Arg Gln Ala Pro Lys Lys Gly Leu Glu Trp Ile
        35                  40                  45

Ala Met Ile Tyr Tyr Asp Ser Ser Lys Met Asn Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Val Pro Thr Ser His Tyr Val Val Asp Val Trp Gly Gln Gly Val
            100                 105                 110

Ser Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly His His His
    210                 215                 220

His His His His His His
225                 230
```

```
<210> SEQ ID NO 11
<211> LENGTH: 492
<212> TYPE: PRT
<213> ORGANISM: Artificial Sequence
<220> FEATURE:
<223> OTHER INFORMATION: GLP-1 anti TfR-fab fusion protein
<220> FEATURE:
<221> NAME/KEY: DISULFID
<222> LOCATION: (70)..(135)
<220> FEATURE:
<221> NAME/KEY: DISULFID
<222> LOCATION: (181)..(241)
```

```
<220> FEATURE:
<221> NAME/KEY: DISULFID
<222> LOCATION: (261)..(481)
<220> FEATURE:
<221> NAME/KEY: DISULFID
<222> LOCATION: (283)..(357)
<220> FEATURE:
<221> NAME/KEY: DISULFID
<222> LOCATION: (407)..(461)

<400> SEQUENCE: 11

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Lys Gly Arg Pro Gly
            20                  25                  30

Gly Gly Ser Gly Gly Gly Ser Gly Gly Gly Ser Gly Gly Gly Ser Asp
        35                  40                  45

Ile Gln Met Thr Gln Ser Pro Ala Ser Leu Ser Ala Ser Leu Glu Glu
65              70                  75                  80

Ile Val Thr Ile Thr Cys Gln Ala Ser Gln Asp Ile Gly Asn Trp Leu
65              70                  75                  80

Ala Trp Tyr Gln Gln Lys Pro Gly Lys Ser Pro Gln Leu Leu Ile Tyr
            85                  90                  95

Gly Ala Thr Ser Leu Ala Asp Gly Val Pro Ser Arg Phe Ser Gly Ser
        100                 105                 110

Arg Ser Gly Thr Gln Phe Ser Leu Lys Ile Ser Arg Val Gln Val Glu
            115                 120                 125

Asp Ile Gly Ile Tyr Tyr Cys Leu Gln Ala Tyr Asn Thr Pro Trp Thr
130             135                 140

Phe Gly Gly Gly Thr Lys Leu Glu Leu Lys Arg Ala Asp Ala Ala Pro
145             150                 155                 160

Thr Val Ser Ile Phe Pro Pro Ser Ser Glu Gln Leu Thr Ser Gly Gly
            165                 170                 175

Ala Ser Val Val Cys Phe Leu Asn Asn Phe Tyr Pro Lys Asp Ile Asn
        180                 185                 190

Val Lys Trp Lys Ile Asp Gly Ser Glu Arg Gln Asn Gly Val Leu Asn
            195                 200                 205

Ser Trp Thr Asp Gln Asp Ser Lys Asp Ser Thr Tyr Ser Met Ser Ser
210             215                 220

Thr Leu Thr Leu Thr Lys Asp Glu Tyr Glu Arg His Asn Ser Tyr Thr
225             230                 235                 240

Cys Glu Ala Thr His Lys Thr Ser Thr Ser Pro Ile Val Lys Ser Phe
            245                 250                 255

Asn Arg Asn Glu Cys Glu Val Gln Leu Val Glu Ser Gly Gly Gly Leu
        260                 265                 270

Val Gln Pro Gly Asn Ser Leu Thr Leu Ser Cys Val Ala Ser Gly Phe
        275                 280                 285

Thr Phe Ser Asn Tyr Gly Met His Trp Ile Arg Gln Ala Pro Lys Lys
        290                 295                 300

Gly Leu Glu Trp Ile Ala Met Ile Tyr Tyr Asp Ser Ser Lys Met Asn
305             310                 315                 320

Tyr Ala Asp Thr Val Lys Gly Arg Phe Thr Ile Ser Arg Asp Asn Ser
            325                 330                 335

Lys Asn Thr Leu Tyr Leu Glu Met Asn Ser Leu Arg Ser Glu Asp Thr
            340                 345                 350

Ala Met Tyr Tyr Cys Ala Val Pro Thr Ser His Tyr Val Val Asp Val
```

-continued

```
                355                 360                 365
Trp Gly Gln Gly Val Ser Val Thr Val Ser Ser Ala Lys Thr Thr Pro
    370                 375                 380
Pro Ser Val Tyr Pro Leu Ala Pro Gly Ser Ala Ala Gln Thr Asn Ser
385                 390                 395                 400
Met Val Thr Leu Gly Cys Leu Val Lys Gly Tyr Phe Pro Glu Pro Val
                405                 410                 415
Thr Val Thr Trp Asn Ser Gly Ser Leu Ser Ser Gly Val His Thr Phe
                420                 425                 430
Pro Ala Val Leu Gln Ser Asp Leu Tyr Thr Leu Ser Ser Ser Val Thr
                435                 440                 445
Val Pro Ser Ser Thr Trp Pro Ser Glu Thr Val Thr Cys Asn Val Ala
            450                 455                 460
His Pro Ala Ser Ser Thr Lys Val Asp Lys Lys Ile Val Pro Arg Asp
465                 470                 475                 480
Cys Gly His His His His His His His His
                485                 490

<210> SEQ ID NO 12
<211> LENGTH: 497
<212> TYPE: PRT
<213> ORGANISM: Artificial Sequence
<220> FEATURE:
<223> OTHER INFORMATION: GLP-1 control Fab fusion protein
<220> FEATURE:
<221> NAME/KEY: DISULFID
<222> LOCATION: (70)..(140)
<220> FEATURE:
<221> NAME/KEY: DISULFID
<222> LOCATION: (186)..(246)
<220> FEATURE:
<221> NAME/KEY: DISULFID
<222> LOCATION: (266)..(486)
<220> FEATURE:
<221> NAME/KEY: DISULFID
<222> LOCATION: (288)..(362)
<220> FEATURE:
<221> NAME/KEY: DISULFID
<222> LOCATION: (411)..(466)

<400> SEQUENCE: 12

His Gly Glu Gly Thr Phe Thr Ser Asp Val Ser Ser Tyr Leu Glu Glu
1               5                   10                  15
Gln Ala Ala Arg Glu Phe Ile Ala Trp Leu Val Lys Gly Arg Pro Gly
                20                  25                  30
Gly Gly Ser Gly Gly Gly Ser Gly Gly Gly Ser Gly Gly Gly Ser Asp
            35                  40                  45
Ile Val Met Thr Gln Thr Pro Leu Ser Leu Ser Val Thr Pro Gly Gln
        50                  55                  60
Pro Ala Ser Ile Ser Cys Arg Ser Ser Gln Ser Leu Leu His Ser Asn
65                  70                  75                  80
Gly Asn Thr Tyr Leu His Trp Tyr Leu Gln Lys Pro Gly Gln Ser Pro
                85                  90                  95
Gln Leu Leu Ile Tyr Lys Val Ser Asn Arg Phe Ser Gly Val Pro Asp
            100                 105                 110
Arg Phe Ser Gly Ser Gly Ser Gly Thr Asp Phe Thr Leu Lys Ile Ser
            115                 120                 125
Arg Val Glu Ala Glu Asp Val Gly Val Tyr Tyr Cys Ser Gln Ser Thr
        130                 135                 140
His Val Pro Trp Thr Phe Gly Gln Gly Thr Lys Val Glu Ile Lys Arg
```

-continued

```
         145                 150                 155                 160
    Thr Val Ala Ala Pro Ser Val Phe Ile Phe Pro Pro Ser Asp Glu Gln
                    165                 170                 175

Leu Lys Ser Gly Thr Ala Ser Val Val Cys Leu Leu Asn Asn Phe Tyr
                    180                 185                 190

Pro Arg Glu Ala Lys Val Gln Trp Lys Val Asp Asn Ala Leu Gln Ser
                    195                 200                 205

Gly Asn Ser Gln Glu Ser Val Thr Glu Gln Asp Ser Lys Asp Ser Thr
                    210                 215                 220

Tyr Ser Leu Ser Ser Thr Leu Thr Leu Ser Lys Ala Asp Tyr Glu Lys
    225                 230                 235                 240

His Lys Val Tyr Ala Cys Glu Val Thr His Gln Gly Leu Ser Ser Pro
                    245                 250                 255

Val Thr Lys Ser Phe Asn Arg Gly Glu Cys Val Gln Leu Val Glu
                    260                 265                 270

Ser Gly Gly Gly Leu Val Gln Pro Gly Asn Ser Leu Thr Leu Ser Cys
                    275                 280                 285

Val Ala Ser Gly Phe Thr Phe Ser Asn Tyr Gly Met His Trp Ile Arg
    290                 295                 300

Gln Ala Pro Lys Lys Gly Leu Glu Trp Ile Ala Met Ile Tyr Tyr Asp
    305                 310                 315                 320

Ser Ser Lys Met Asn Tyr Ala Asp Thr Val Lys Gly Arg Phe Thr Ile
                    325                 330                 335

Ser Arg Asp Asn Ser Lys Asn Thr Leu Tyr Leu Glu Met Asn Ser Leu
                    340                 345                 350

Arg Ser Glu Asp Thr Ala Met Tyr Tyr Cys Ala Val Pro Thr Ser His
                    355                 360                 365

Tyr Val Val Asp Val Trp Gly Gln Gly Val Ser Val Thr Val Ser Ser
                    370                 375                 380

Ala Lys Thr Thr Pro Pro Ser Val Tyr Pro Leu Ala Pro Gly Ser Ala
    385                 390                 395                 400

Ala Gln Thr Asn Ser Met Val Thr Leu Gly Cys Leu Val Lys Gly Tyr
                    405                 410                 415

Phe Pro Glu Pro Val Thr Val Thr Trp Asn Ser Gly Ser Leu Ser Ser
                    420                 425                 430

Gly Val His Thr Phe Pro Ala Val Leu Gln Ser Asp Leu Tyr Thr Leu
                    435                 440                 445

Ser Ser Ser Val Thr Val Pro Ser Ser Thr Trp Pro Ser Glu Thr Val
    450                 455                 460

Thr Cys Asn Val Ala His Pro Ala Ser Ser Thr Lys Val Asp Lys Lys
    465                 470                 475                 480

Ile Val Pro Arg Asp Cys Gly His His His His His His His His
                    485                 490                 495

His
```

<210> SEQ ID NO 13
<211> LENGTH: 52
<212> TYPE: PRT
<213> ORGANISM: Artificial Sequence
<220> FEATURE:
<223> OTHER INFORMATION: GLP-1 analogue with C-terminal peptidic linker
<220> FEATURE:
<221> NAME/KEY: MOD_RES
<222> LOCATION: (2)..(2)
<223> OTHER INFORMATION: Aib

```
<400> SEQUENCE: 13

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Gly
            20                  25                  30

Gln Ala Pro Gly Gln Ala Pro Gly Gln Ala Pro Gly Gln Ala Pro Gly
        35                  40                  45

Gln Ala Pro Lys
    50

<210> SEQ ID NO 14
<211> LENGTH: 21
<212> TYPE: PRT
<213> ORGANISM: Artificial Sequence
<220> FEATURE:
<223> OTHER INFORMATION: Peptidic linker

<400> SEQUENCE: 14

Gly Gln Ala Pro Gly Gln Ala Pro Gly Gln Ala Pro Gly Gln Ala Pro
1               5                   10                  15

Gly Gln Ala Pro Lys
            20

<210> SEQ ID NO 15
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 15

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Gly
            20                  25                  30

<210> SEQ ID NO 16
<211> LENGTH: 31
<212> TYPE: PRT
<213> ORGANISM: Homo sapiens

<400> SEQUENCE: 16

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 17
<211> LENGTH: 16
<212> TYPE: PRT
<213> ORGANISM: Artificial Sequence
<220> FEATURE:
<223> OTHER INFORMATION: Signal peptide

<400> SEQUENCE: 17

Met Pro Leu Leu Leu Leu Leu Pro Leu Leu Trp Ala Gly Ala Leu Ala
1               5                   10                  15

<210> SEQ ID NO 18
<211> LENGTH: 4
<212> TYPE: PRT
<213> ORGANISM: Artificial Sequence
<220> FEATURE:
```

```
<223> OTHER INFORMATION: peptidic linker

<400> SEQUENCE: 18

Gly Gly Gly Ser
1
```